United States Patent
Farritor et al.

(10) Patent No.: US 9,060,781 B2
(45) Date of Patent: Jun. 23, 2015

(54) METHODS, SYSTEMS, AND DEVICES RELATING TO SURGICAL END EFFECTORS

(75) Inventors: Shane Farritor, Lincoln, NE (US); Tom Frederick, Lincoln, NE (US); Joe Bartels, Lincoln, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 265 days.

(21) Appl. No.: 13/493,725

(22) Filed: Jun. 11, 2012

(65) Prior Publication Data
US 2013/0041360 A1 Feb. 14, 2013

Related U.S. Application Data

(60) Provisional application No. 61/495,487, filed on Jun. 10, 2011, provisional application No. 61/498,919, filed on Jun. 20, 2011.

(51) Int. Cl.
| | |
|---|---|
| *A61B 18/18* | (2006.01) |
| *A61B 18/14* | (2006.01) |
| *A61B 19/00* | (2006.01) |
| *A61B 18/00* | (2006.01) |

(52) U.S. Cl.
CPC ......... *A61B 18/1445* (2013.01); *A61B 19/2203* (2013.01); *A61B 2018/00345* (2013.01); *A61B 2018/0063* (2013.01); *A61B 2018/1455* (2013.01)

(58) Field of Classification Search
USPC ............................................ 606/33, 130, 170
See application file for complete search history.

(56) References Cited

U.S. PATENT DOCUMENTS

| | | | |
|---|---|---|---|
| 3,870,264 | A | 3/1975 | Robinson |
| 3,989,952 | A | 11/1976 | Hohmann |
| 4,246,661 | A | 1/1981 | Pinson |
| 4,258,716 | A | 3/1981 | Sutherland |
| 4,278,077 | A | 7/1981 | Mizumoto |
| 4,538,594 | A | 9/1985 | Boebel et al. |

(Continued)

FOREIGN PATENT DOCUMENTS

| | | |
|---|---|---|
| EP | 2286756 A1 | 2/2011 |
| JP | 2004144533 | 5/1990 |

(Continued)

OTHER PUBLICATIONS

Tendick et al., "Applications of Micromechatronics in Minimally Invasive Surgery," IEEE/ASME Transactions on Mechatronics, 1998; 3(1): 34-42.

(Continued)

*Primary Examiner* — Carl H Layno
*Assistant Examiner* — Jon Eric C Morales
(74) *Attorney, Agent, or Firm* — Davis, Brown, Koehn, Shors & Roberts, P.C.; Sean D. Solberg

(57) ABSTRACT

The embodiments disclosed herein relate to various medical device components, including components that can be incorporated into robotic and/or in vivo medical devices, and more specifically including end effectors that can be incorporated into such devices. Certain end effector embodiments include various vessel cautery devices that have rotational movement as well as cautery and cutting functions while maintaining a relatively compact structure. Other end effector embodiments include various dual end effector devices that have more than one end effector.

20 Claims, 23 Drawing Sheets

(56) References Cited

U.S. PATENT DOCUMENTS

| | | |
|---|---|---|
| 4,568,311 A | 2/1986 | Miyake |
| 4,623,183 A | 11/1986 | Amori |
| 4,736,645 A | 4/1988 | Zimmer |
| 4,771,652 A | 9/1988 | Zimmer |
| 4,852,391 A | 8/1989 | Ruch et al. |
| 4,896,015 A | 1/1990 | Taboada et al. |
| 4,897,014 A | 1/1990 | Tietze |
| 4,922,755 A | 5/1990 | Oshiro et al. |
| 4,990,050 A | 2/1991 | Tsuge et al. |
| 5,019,968 A | 5/1991 | Wang et al. |
| 5,108,140 A | 4/1992 | Bartholet |
| 5,172,639 A | 12/1992 | Wiesman et al. |
| 5,176,649 A | 1/1993 | Wakabayashi |
| 5,178,032 A | 1/1993 | Zona et al. |
| 5,187,032 A | 2/1993 | Sasaki et al. |
| 5,187,796 A | 2/1993 | Wang et al. |
| 5,195,388 A | 3/1993 | Zona et al. |
| 5,201,325 A | 4/1993 | McEwen et al. |
| 5,217,003 A | 6/1993 | Wilk |
| 5,263,382 A | 11/1993 | Brooks et al. |
| 5,271,384 A | 12/1993 | McEwen et al. |
| 5,284,096 A | 2/1994 | Pelrine et al. |
| 5,297,443 A | 3/1994 | Wentz |
| 5,297,536 A | 3/1994 | Wilk |
| 5,304,899 A | 4/1994 | Sasaki et al. |
| 5,307,447 A | 4/1994 | Asano et al. |
| 5,353,807 A | 10/1994 | DeMarco |
| 5,363,935 A | 11/1994 | Schempf et al. |
| 5,382,885 A | 1/1995 | Salcudean et al. |
| 5,388,528 A | 2/1995 | Pelrine et al. |
| 5,436,542 A | 7/1995 | Petelin et al. |
| 5,441,494 A | 8/1995 | Ortiz |
| 5,458,131 A | 10/1995 | Wilk |
| 5,458,583 A | 10/1995 | McNeely et al. |
| 5,458,598 A | 10/1995 | Feinberg et al. |
| 5,471,515 A | 11/1995 | Fossum et al. |
| 5,515,478 A | 5/1996 | Wang |
| 5,524,180 A | 6/1996 | Wang et al. |
| 5,553,198 A | 9/1996 | Wang et al. |
| 5,562,448 A | 10/1996 | Mushabac |
| 5,588,442 A | 12/1996 | Scovil et al. |
| 5,620,417 A | 4/1997 | Jang et al. |
| 5,623,582 A | 4/1997 | Rosenberg |
| 5,624,398 A | 4/1997 | Smith et al. |
| 5,632,761 A | 5/1997 | Smith et al. |
| 5,645,520 A | 7/1997 | Nakamura et al. |
| 5,657,429 A | 8/1997 | Wang et al. |
| 5,657,584 A | 8/1997 | Hamlin |
| 5,672,168 A | 9/1997 | de la Torre et al. |
| 5,674,030 A | 10/1997 | Sigel |
| 5,728,599 A | 3/1998 | Rosteker et al. |
| 5,736,821 A | 4/1998 | Suyama et al. |
| 5,754,741 A | 5/1998 | Wang et al. |
| 5,762,458 A | 6/1998 | Wang et al. |
| 5,769,640 A | 6/1998 | Jacobus et al. |
| 5,791,231 A | 8/1998 | Cohn et al. |
| 5,792,135 A | 8/1998 | Madhani et al. |
| 5,797,900 A | 8/1998 | Madhani et al. |
| 5,807,377 A | 9/1998 | Madhani et al. |
| 5,815,640 A | 9/1998 | Wang et al. |
| 5,825,982 A | 10/1998 | Wright et al. |
| 5,841,950 A | 11/1998 | Wang et al. |
| 5,845,646 A | 12/1998 | Lemelson |
| 5,855,583 A | 1/1999 | Wang et al. |
| 5,876,325 A | 3/1999 | Mizuno et al. |
| 5,878,193 A | 3/1999 | Wang et al. |
| 5,878,783 A | 3/1999 | Smart |
| 5,895,417 A | 4/1999 | Pomeranz et al. |
| 5,906,591 A | 5/1999 | Dario et al. |
| 5,907,664 A | 5/1999 | Wang et al. |
| 5,911,036 A | 6/1999 | Wright et al. |
| 5,971,976 A | 10/1999 | Wang et al. |
| 6,001,108 A | 12/1999 | Wang et al. |
| 6,007,550 A | 12/1999 | Wang et al. |
| 6,030,365 A | 2/2000 | Laufer |
| 6,031,371 A | 2/2000 | Smart |
| 6,058,323 A | 5/2000 | Lemelson |
| 6,063,095 A | 5/2000 | Wang et al. |
| 6,066,090 A | 5/2000 | Yoon |
| 6,102,850 A | 8/2000 | Wang et al. |
| 6,107,795 A | 8/2000 | Smart |
| 6,132,368 A | 10/2000 | Cooper |
| 6,132,441 A | 10/2000 | Grace |
| 6,156,006 A | 12/2000 | Brosens et al. |
| 6,159,146 A | 12/2000 | El Gazayerli |
| 6,162,171 A | 12/2000 | Ng et al. |
| D438,617 S | 3/2001 | Cooper et al. |
| 6,206,903 B1 | 3/2001 | Ramans |
| D441,076 S | 4/2001 | Cooper et al. |
| 6,223,100 B1 | 4/2001 | Green |
| D441,862 S | 5/2001 | Cooper et al. |
| 6,238,415 B1 | 5/2001 | Sepetka et al. |
| 6,240,312 B1 | 5/2001 | Alfano et al. |
| 6,241,730 B1 | 6/2001 | Alby |
| 6,244,809 B1 | 6/2001 | Wang et al. |
| 6,246,200 B1 | 6/2001 | Blumenkranz et al. |
| D444,555 S | 7/2001 | Cooper et al. |
| 6,286,514 B1 | 9/2001 | Lemelson |
| 6,292,678 B1 | 9/2001 | Hall et al. |
| 6,293,282 B1 | 9/2001 | Lemelson |
| 6,296,635 B1 | 10/2001 | Smith et al. |
| 6,309,397 B1 | 10/2001 | Julian et al. |
| 6,309,403 B1 | 10/2001 | Minoret et al. |
| 6,312,435 B1 | 11/2001 | Wallace et al. |
| 6,321,106 B1 | 11/2001 | Lemelson |
| 6,327,492 B1 | 12/2001 | Lemelson |
| 6,331,181 B1 | 12/2001 | Tierney et al. |
| 6,346,072 B1 | 2/2002 | Cooper |
| 6,352,503 B1 | 3/2002 | Matsui et al. |
| 6,364,888 B1 | 4/2002 | Niemeyer et al. |
| 6,371,952 B1 | 4/2002 | Madhani et al. |
| 6,394,998 B1 | 5/2002 | Wallace et al. |
| 6,398,726 B1 | 6/2002 | Ramans et al. |
| 6,400,835 B1 | 6/2002 | Lemelson |
| 6,400,980 B1 | 6/2002 | Lemelson |
| 6,424,885 B1 | 7/2002 | Niemeyer et al. |
| 6,432,112 B2 | 8/2002 | Brock et al. |
| 6,436,107 B1 | 8/2002 | Wang et al. |
| 6,441,577 B2 | 8/2002 | Blumenkranz et al. |
| 6,450,104 B1 | 9/2002 | Grant et al. |
| 6,451,027 B1 | 9/2002 | Cooper et al. |
| 6,454,758 B1 | 9/2002 | Thompson et al. |
| 6,459,926 B1 | 10/2002 | Nowlin et al. |
| 6,463,361 B1 | 10/2002 | Wang et al. |
| 6,468,203 B2 | 10/2002 | Belson |
| 6,468,265 B1 | 10/2002 | Evans et al. |
| 6,470,236 B2 | 10/2002 | Ohtsuki |
| 6,491,691 B1 | 12/2002 | Morley et al. |
| 6,491,701 B2 | 12/2002 | Tierney et al. |
| 6,493,608 B1 | 12/2002 | Niemeyer et al. |
| 6,496,099 B2 | 12/2002 | Wang et al. |
| 6,508,413 B2 | 1/2003 | Bauer et al. |
| 6,512,345 B2 | 1/2003 | Borenstein |
| 6,522,906 B1 | 2/2003 | Salisbury, Jr. et al. |
| 6,544,276 B1 | 4/2003 | Azizi |
| 6,548,982 B1 | 4/2003 | Papanikolopoulos et al. |
| 6,554,790 B1 | 4/2003 | Moll |
| 6,565,554 B1 | 5/2003 | Niemeyer |
| 6,574,355 B2 | 6/2003 | Green |
| 6,587,750 B2 | 7/2003 | Gerbi et al. |
| 6,591,239 B1 | 7/2003 | McCall et al. |
| 6,594,552 B1 | 7/2003 | Nowlin et al. |
| 6,610,007 B2 | 8/2003 | Belson et al. |
| 6,620,173 B2 | 9/2003 | Gerbi et al. |
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |

(56) References Cited

U.S. PATENT DOCUMENTS

| | | |
|---|---|---|
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et al. |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,021,358 B2 | 9/2011 | Doyle et al. |
| 8,179,073 B2 | 5/2012 | Farritor et al. |
| 8,353,897 B2 | 1/2013 | Doyle et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 | 2/2002 | Woloszka et al. |
| 2002/0038077 A1 | 3/2002 | de la Torre et al. |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julien et al. |
| 2002/0128552 A1 | 9/2002 | Nowlin et al. |
| 2002/0140392 A1 | 10/2002 | Borenstein et al. |
| 2002/0147487 A1 | 10/2002 | Sundquist et al. |

(56) References Cited

U.S. PATENT DOCUMENTS

| | | |
|---|---|---|
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0102772 A1 | 5/2004 | Baxter et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1 | 6/2007 | Hardin et al. |
| 2007/0156019 A1 | 7/2007 | Larkin et al. |
| 2007/0156211 A1 | 7/2007 | Ferren et al. |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Oleynikov et al. |
| 2007/0244520 A1 | 10/2007 | Ferren et al. |
| 2007/0250064 A1 | 10/2007 | Darois et al. |
| 2007/0255273 A1 | 11/2007 | Fernandez et al. |
| 2008/0004634 A1 | 1/2008 | Farritor |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor |
| 2008/0058989 A1 | 3/2008 | Oleynikov |
| 2008/0103440 A1 | 5/2008 | Ferren et al. |
| 2008/0111513 A1 | 5/2008 | Farritor |
| 2008/0119870 A1* | 5/2008 | Williams ..................... 606/130 |
| 2008/0132890 A1 | 6/2008 | Woloszko et al. |
| 2008/0161804 A1 | 7/2008 | Rioux et al. |
| 2008/0164079 A1 | 7/2008 | Jacobsen |
| 2008/0183033 A1 | 7/2008 | Bern et al. |
| 2008/0221591 A1 | 9/2008 | Farritor |
| 2008/0269557 A1 | 10/2008 | Marescaux et al. |
| 2008/0269562 A1 | 10/2008 | Marescaux et al. |
| 2009/0020724 A1 | 1/2009 | Paffrath |
| 2009/0024142 A1 | 1/2009 | Ruiz Morales |
| 2009/0048612 A1 | 2/2009 | Farritor |
| 2009/0054909 A1 | 2/2009 | Farritor |
| 2009/0069821 A1 | 3/2009 | Farritor et al. |
| 2009/0076536 A1 | 3/2009 | Rentschler |
| 2009/0137952 A1 | 5/2009 | Ramamurthy et al. |
| 2009/0143787 A9 | 6/2009 | De La Pena |
| 2009/0163929 A1 | 6/2009 | Yeung et al. |
| 2009/0171373 A1 | 7/2009 | Farritor |
| 2009/0234369 A1 | 9/2009 | Bax et al. |
| 2009/0236400 A1 | 9/2009 | Cole et al. |
| 2009/0240246 A1* | 9/2009 | Deville et al. ................. 606/33 |
| 2009/0247821 A1 | 10/2009 | Rogers |
| 2009/0248038 A1 | 10/2009 | Blumenkranz et al. |
| 2009/0281377 A1 | 11/2009 | Newell et al. |
| 2009/0305210 A1 | 12/2009 | Guru et al. |
| 2010/0010294 A1 | 1/2010 | Conlon et al. |
| 2010/0016659 A1 | 1/2010 | Weitzner et al. |
| 2010/0016853 A1 | 1/2010 | Burbank |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1* | 8/2010 | Scott ............................ 606/130 |
| 2010/0204713 A1 | 8/2010 | Ruiz |
| 2010/0245549 A1 | 9/2010 | Allen et al. |
| 2010/0262162 A1 | 10/2010 | Omori |
| 2010/0292691 A1 | 11/2010 | Brogna |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0071544 A1 | 3/2011 | Steger et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor |
| 2011/0238080 A1 | 9/2011 | Ranjit et al. |
| 2011/0270443 A1 | 11/2011 | Kamiya et al. |
| 2012/0035582 A1 | 2/2012 | Nelson et al. |
| 2012/0109150 A1 | 5/2012 | Quaid et al. |
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |

(56) References Cited

U.S. PATENT DOCUMENTS

FOREIGN PATENT DOCUMENTS

| | | |
|---|---|---|
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| WO | WO 92/21291 | 12/1992 |
| WO | WO 02/082979 | 10/2002 |
| WO | WO 02/100256 | 12/2002 |
| WO | WO 2005/009211 | 2/2005 |
| WO | WO 2006 005075 | 1/2006 |
| WO | WO 2006/079108 | 1/2006 |
| WO | WO 2006/052927 | 5/2006 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO 2011/118646 A1 | 9/2011 |
| WO | WO 2011/135503 A1 | 11/2011 |
| WO | WO 2013009887 | 1/2013 |

OTHER PUBLICATIONS

Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.
Wolfe et al., "Endoscopic Cholecystectomy: An analysis of Complications," Arch. Surg. Oct. 1991; 126: 1192-1196.
Worn et al., "Espirit Project No. 33915: Miniaturised Robot for Micro Manipulation (MINIMAN)", Nov. 1998; http://www.ipr.ira.ujka.de/-microbot/miniman.
Yu et al., "Microrobotic Cell Injection," Proceedings of the 2001 IEEE International Conference on Robotics and Automation, May 2001; 620-625.
Yu, BSN, RN, "M2ATM Capsule Endoscopy A Breakthrough Diagnostic Tool for Small Intestine Imagining," vol. 25, No. 1, Gastroenterology Nursing, pp. 24-27.
International Search Report and Written Opinion of international application No. PCT/US2010/061137, mailed Feb. 11, 2011, 10 pp.
Abbou et al., "Laparoscopic Radical Prostatectomy with a Remote Controlled Robot," The Journal of Urology, Jun. 2001, 165: 1964-1966.
Glukhovsky et al.., "The development and application of wireless capsule endoscopy," Int. J. Med. Robot. Comput. Assist. Surgery, 2004; I (1): 114-123.
Gong et al., "Wireless endoscopy," Gastrointestinal Endoscopy 2000; 51(6): 725-729.
Hanly et al., "Value of the SAGES Learning Center in introducing new technology," Surgical Endoscopy, 2004; 19 (4): 477-483.

Hanly et al., "Robotic Abdominal Surgery," The American Journal of Surgery 188 (Suppl.to Oct. 1994): 19S-26S, 2004.
International Preliminary Report on Patentability from related case PCT/US2007/014567, mailed Jan. 8, 2009, 11 pp.
International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
"International Search Report and Written Opinion from international application No. PCT/US07/14567, mailed Apr. 28, 2008, 19 pp.".
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.

(56) References Cited

OTHER PUBLICATIONS

Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, 1/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Miller, Ph.D., et al., "In-Vivo Stereoscopic Imaging System with 5 Degrees-of-Freedom for Minimal Access Surgery," Dept. of Computer Science and Dept. of Surgery, Columbia University, New York, NY, 7 pp.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Palm, William, "Rapid Prototyping Primer" May 1998 (revised Jul. 30, 2002) (http://www.me.psu.edu/lamancusa/rapidpro/primer/chapter2.htm).
Patronik et al., "Development of a Tethered Epicardial Crawler for Minimally Invasive Cardiac Therapies," IEEE, pp. 239-240.
Patronik et al., "Crawling on the Heart: A Mobile Robotic Device for Minimally Invasive Cardiac Interventions," MICCAI, 2004, pp. 9-16.
Patronik et al., "Preliminary evaluation of a mobile robotic device for navigation and intervention on the beating heart," Computer Aided Surgery, 10(4): 225-232, Jul. 2005.
Peirs et al., "A miniature manipulator for integration in a self-propelling endoscope," Sensors and Actuators A, 2001, 92: 343-349.
Peters, "Minimally Invasive Colectomy: Are the Potential Benefits Realized?" Dis Colon Rectum 1993; 36: 751-756.
Phee et al., "Analysis and Development of Locomotion Devices for the Gastrointestinal Tract," IEEE Transaction on Biomedical Engineering, vol. 49, No. 6, Jun. 2002, pp. 613-616.
Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.
Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.
Preliminary Amendment filed Apr. 11, 2007, in related case U.S. Appl. No. 11/403,756, 7 pp.
Preliminary Amendment filed Jul. 30, 2008, in related case U.S. Appl. No. 12/171,413, 4 pp.
RCE and Amendment filed Jun. 13, 2007, in related case U.S. Appl. No. 11/403,756, 8 pp.
Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.
Rentschler et al., "Mobile In Vivo Biopsy Robot," IEEE International Conference on Robotics and Automation, Orlando, Florida, May 2006, pp. 4155-4160.
Rentschler et al., "Miniature in vivo Robots for Remote and Harsh Environments," IEEE Transactions on Information Technology in Biomedicine, Jan. 2006; 12(1): 66-75.
Rentschler et al., "An In Vivo Mobile Robot for Surgical Vision and Task Assistance," Journal of Medical Devices, Mar. 2007, vol. 1: 23-29.
Rentschler et al., "In vivo Mobile Surgical Robotic Task Assistance," 1 pg.
Rentschler et al., "In vivo Robotics during the NEEMO 9 Mission," Medicine Meets Virtual Reality, Feb. 2007, I pg.
Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.
Rentschler et al., "Mechanical Design of Robotic In Vivo Wheeled Mobility," ASME Journal of Mechanical Design, 2006a, pp. I-II.
Rentschler et al., "Mobile In Vivo Camera Robots Provide Sole Visual Feedback for Abdominal Exploration and Cholecystectomy," Journal of Surgical Endoscopy, 20-I: 135-138, 2006b.
Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.
Rentschler et al., "Modeling, Analysis, and Experimental Study of In Vivo Wheeled Robotic Mobility," IEEE Transactions on Robotics, 22 (2): 308-321, 2005c.
Rentschler et al., "Natural Orifice Surgery with an Endoluminal Mobile Robot," The Society of American Gastrointestinal Endoscopic Surgeons, Dallas, TX, Apr. 2006d, 14 pp.
Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.
Rentschler et al., "Toward In Vivo Mobility," Studies in Health Technology and Infonnatics—Medicine Meets Virtual Reality, ISO Press, Long Beach, CA, 2005a, III: 397-403.
Response to Rule 312 Amendment in related case U.S. Appl. No. 11/695,944, dated Jan. 12, 2009, 2 pp.
Riviere et al., "Toward Active Tremor Canceling in Handheld Microsurgical Instruments," IEEE Transactions on Robotics and Automation, Oct. 2003, 19(5): 793-800.
Rosen et al., "Force Controlled and Teleoperated Endoscopic, Grasper for Minimally Invasive Surgery-Experimental Performance Evaluation," IEEE Transactions of Biomedical Engineering, Oct. 1999; 46(10): 1212-1221.
Rosen et al., "Objective Laparoscopic Skills Assessments of Surgical Residents Using Hidden Markov Models Based on Haptic Information and Tool/Tissue Interactions," Studies in Health Technology and Infonnatics—Medicine Meets Virtual Reality, Jan. 2001, 7 pp.
Rosen et al., "Spherical Mechanism Analysis of a Surgical Robot for Minimally Invasive Surgery—Analytical and Experimental

(56) References Cited

OTHER PUBLICATIONS

Approaches," Studies in Health Technology and Infonnatics—Medicine Meets Virtual Reality, pp. 442-448, Jan. 2005.
Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.
Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.
Ruurda et al., "Robot-Assisted surgical systems: a new era in laparoscopic surgery," Ann R. Coll Surg Engl., 2002; 84: 223-226.
Ruurda et al., "Feasibility of Robot-Assisted Laparoscopic Surgery," Surgical Laparoscopy, Endoscopy & Percutaneous Techniques, 2002; 12(1):41-45.
Sackier et al., "Robotically assisted laparoscopic surgery," Surgical Endoscopy, 1994; 8: 63-66.
Salky, "What is the Penetration of Endoscopic Techniques into Surgical Practice?" Digestive Surgery, 2000; 17:422-426.
Satava, "Surgical Robotics: The Early Chronicles," Surgical Laparoscopy, Endoscopy & Percutaneous Techniques, 2002; 12(1): 6-16.
Schippers et al., (1996) "Requirements and Possibilities of Computer-Assisted Endoscopic Surgery," In: Computer Integrated Surgery: Technology and Clinical Applications, pp. 561-565.
Schurr et al., "Robotics and Telemanipulation Technologies for Endoscopic Surgery," Surgical Endoscopy, 2000; 14: 375-381.
Schwartz, "In the Lab: Robots that Slink and Squirm," The New York Times, Mar. 27, 2007, 4 pp.
Sharp LL-151-3D, http://www.sharp3d.com, 2006, 2 pp.
Slatkin et al., "The Development of a Robotic Endoscope," Proceedings of the 1995 IEEE International Conference on Robotics and Automation, pp. 162-171, 1995.
Smart Pill "Fantastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.

Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al., "Telesurgery and Surgical Simulation: Haptic Interfaces to Real and Virtual Surgical Environments," In McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.

(56) References Cited

OTHER PUBLICATIONS

Fireman et al., "Diagnosing small bowel Crohn's desease with wireless capsule endoscopy," Gut 2003; 52: 390-392.

Flynn et al., "Tomorrow's Surgery: micromotors and microbots for minimally invasive procedures," Minimally Invasive Surgery & Allied Technologies.

Franklin et al., "Prospective Comparison of Open vs. Laparoscopic Colon Surgery for Carcinoma: Five-Year Results," Dis Colon Rectum, 1996; 39: S35-S46.

Franzino, "The Laprotek Surgical System and the Next Generation of Robotics," Surg Clin North Am, 2003 83(6): 1317-1320.

Fraulob et al., "Miniature assistance module for robot-assisted heart surgery," Biomed. Tech. 2002, 47 Suppl. 1, Pt. 1: 12-15.

Fukuda et al., "Mechanism and Swimming Experiment of Micro Mobile Robot in Water," Proceedings of the 1994 IEEE International Conference on Robotics and Automation, 1994: 814-819.

Fukuda et al., "Micro Active Catheter System with Multi Degrees of Freedom," Proceedings of the IEEE International Conference on Robotics and Automation, May 1994, pp. 2290-2295.

Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.

Grady, "Doctors Try New Surgery for Gallbladder Removal," The New York Times, Apr. 20, 2007, 3 pp.

Guber et al., "Miniaturized Instrumetn Systems for Minimally Invasive Diagnosis and Therapy," Biomedizinishe Technic. 2002, Band 47, Erganmngsband 1: 1-4.

\* cited by examiner

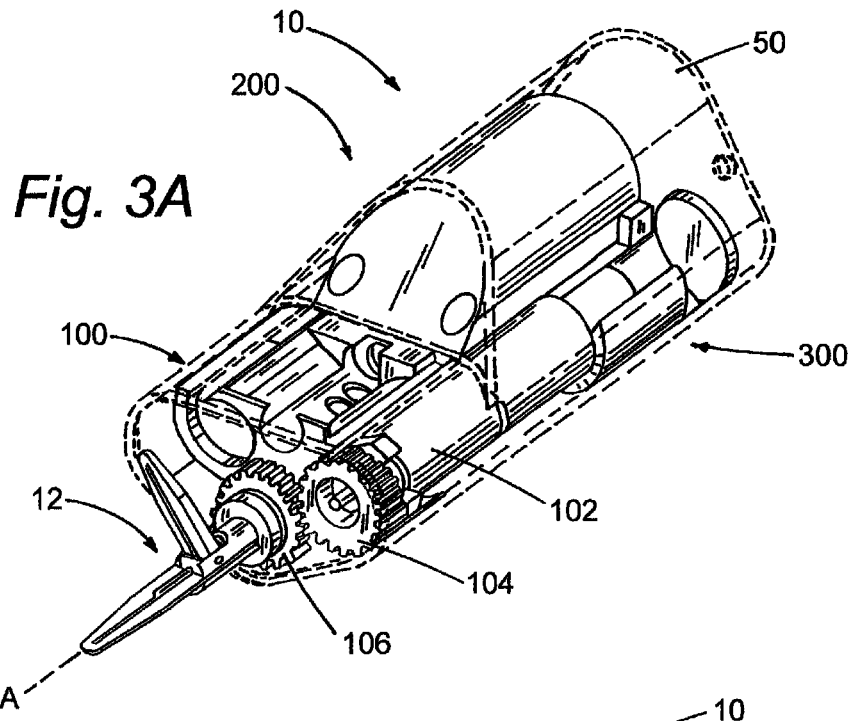
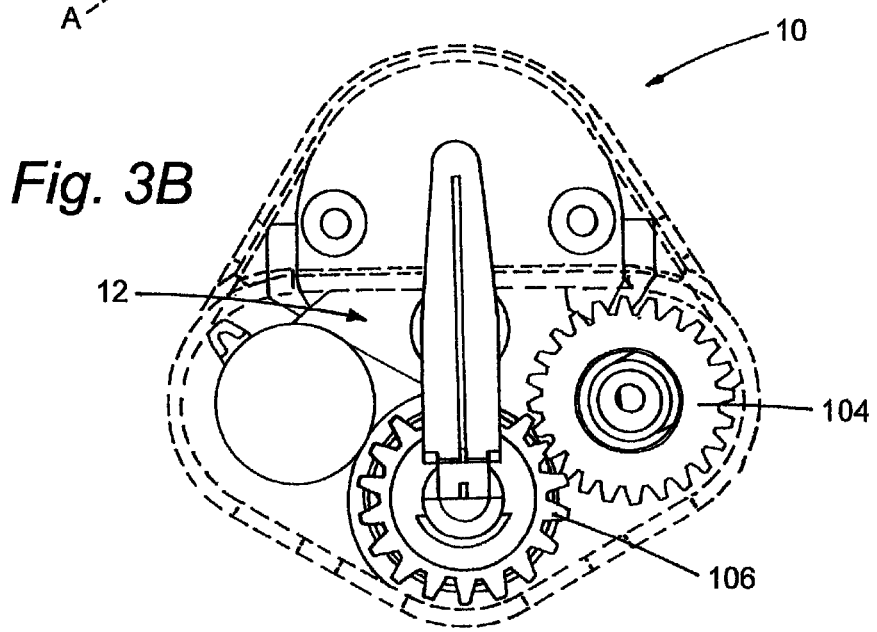

METHODS, SYSTEMS, AND DEVICES RELATING TO SURGICAL END EFFECTORS

CROSS-REFERENCE TO RELATED APPLICATION(S)

This application claims the benefit under 35 U.S.C. §119 (e) to U.S. Provisional Patent application 61/495,487, filed Jun. 10, 2011, entitled "Vessel Sealing Device for Robotic Devices," and to U.S. Provisional Patent Application 61/498,919, filed Jun. 20, 2011, entitled "Dual End Effector Components and Related Devices, Systems, and Methods," both of which are incorporated herein by reference in their entireties.

GOVERNMENT SUPPORT

This invention was made with government support under at least one of the following grants: Grant Nos. NNX10AJ26G and NNX09AO71A, awarded by the National Aeronautics and Space Administration; Grants Nos. W81XWH-08-2-0043 and W81XWH-09-2-0185, awarded by U.S. Army Medical Research and Materiel Command; Grant No. DGE-1041000, awarded by the National Science Foundation; and Grant No. 2009-147-SC1, awarded by the Experimental Program to Stimulate Competitive Research at National Aeronautics and Space Administration. Accordingly, the government has certain right in the invention.

FIELD OF THE INVENTION

The embodiments disclosed herein relate to various medical device components and related components, including robotic and/or in vivo medical devices and related components. More specifically, certain embodiments include various medical device attachment and control components, often referred to as "end effectors" or "operational components." Certain end effector embodiments disclosed herein include vessel sealing and cutting devices, and, in particular, bipolar cautery devices having integrated cutting components. Other end effector embodiments disclosed herein include various dual end effector components, wherein such components have two or more end effectors. Further embodiments relate to systems and methods for operating the above components.

BACKGROUND OF THE INVENTION

Invasive surgical procedures are essential for addressing various medical conditions. When possible, minimally invasive procedures, such as laparoscopy, are preferred.

However, known minimally invasive technologies such as laparoscopy are limited in scope and complexity due in part to the need to remove and insert new surgical tools into the body cavity when changing surgical instruments due to the size of access ports. Known robotic systems such as the da Vince® Surgical System (available from Intuitive Surgical, Inc., located in Sunnyvale, Calif.) are also restricted by the access ports, the necessity for medical professionals to remove and insert new surgical tools into the abdominal cavity, as well as having the additional disadvantages of being very large, very expensive, unavailable in most hospitals, and having limited sensory and mobility capabilities.

There is a need in the art for improved surgical methods, systems, and devices.

BRIEF SUMMARY OF THE INVENTION

Discussed herein are various surgical end effectors—including certain cauterizing end effectors and certain dual end effector—for use in surgical devices, including robotic in vivo devices.

In Example 1, an in vivo vessel sealing device comprises a device body and a bipolar vessel cautery component operably coupled to the device body. The device body has a cautery component actuation motor, a cutting component actuation motor, a jaw actuation motor, and a cautery component shaft disposed within the body and operably coupled to the jaw actuation motor. The cautery component has a stationary jaw coupled to a distal end of the cautery component shaft, a mobile jaw pivotally coupled to the distal end of the cautery component shaft, and a cutting component operably coupled to the cutting component actuation motor. In addition, the cautery component is operably coupled to the cautery component actuation motor.

Example 2 relates to the sealing device according to Example 1, wherein the cautery component is rotatable about an axis parallel with the shaft.

Example 3 relates to the sealing device according to Example 1, wherein the overall length of the device body is under about 3 inches.

Example 4 relates to the sealing device of Example 1, wherein the overall length of the cautery component is under about 1.5 inches.

Example 5 relates to the sealing device of Example 1, wherein the device is an end effector coupled to an arm of an in vivo robotic device.

Example 6 relates to an in vivo robotic device comprising a device body operably coupled to at least one arm, wherein the sealing device of Example 1 is operably coupled to the at least one arm.

In Example 7, a method of cauterizing tissue of a patient with an in vivo cautery device comprises positioning an in vivo cautery device near the tissue, positioning a cautery component rotationally in relation to the tissue with a cautery component actuation motor, and opening a mobile jaw with a jaw actuation motor and positioning the cautery component such that the tissue is positioned between the mobile and stationary jaws. The method further comprises closing the mobile jaw with a jaw actuation motor, applying an electrical current to the tissue via the mobile and stationary jaws, thereby cauterizing the tissue, and urging the cutting component in a distal direction with the cutting component actuation motor, thereby cutting the cauterized tissue positioned between the mobile and stationary jaws.

In Example 8, an operational component for an in vivo surgical device comprises an actuator housing comprising at least one actuator; and an end effector housing operably coupled to the actuator housing. The end effector housing comprises a first end effector rotationally coupled to the end effector housing and a second end effector rotationally coupled to the end effector housing.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3A is a perspective view of a vessel sealing device with the exterior shown transparent to reveal inner components, according to one embodiment.

FIG. 3B is a front view of a vessel sealing device with the exterior shown transparent to reveal inner components, according to one embodiment.

DETAILED DESCRIPTION

Figure 1A:
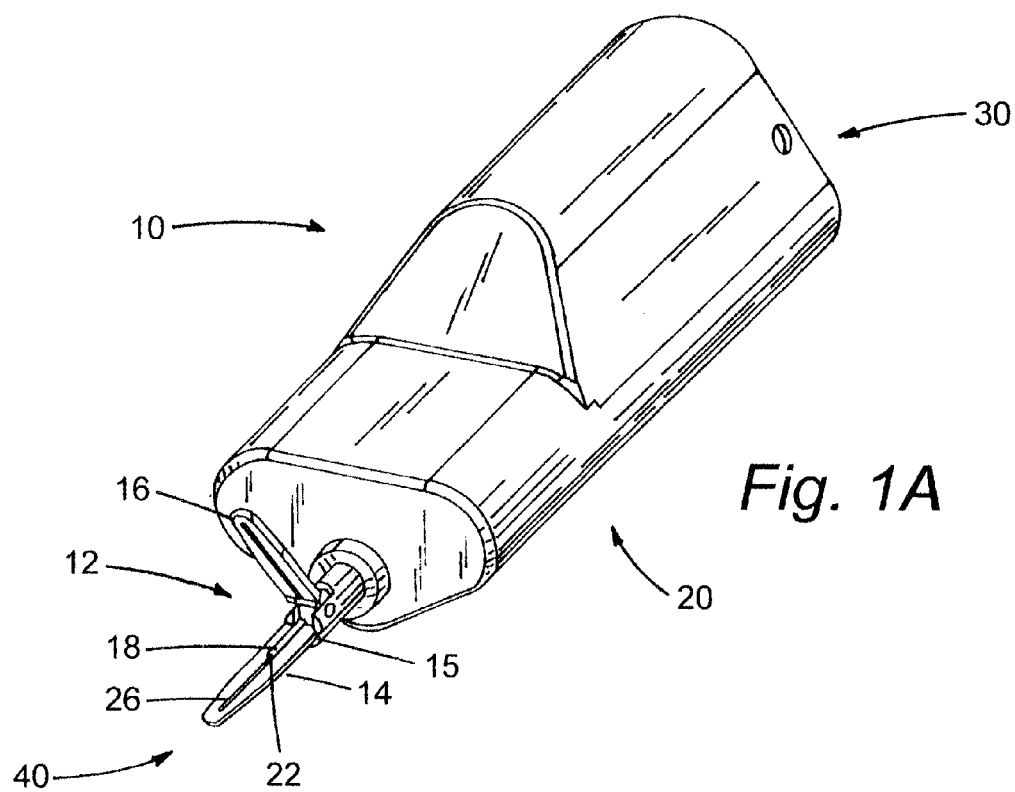
FIG. 1A is a perspective view of a vessel sealing device, according to one embodiment.

The various systems and devices disclosed herein relate to devices for use in medical procedures and systems. More specifically, various embodiments relate to end effector devices that can be used in various procedural devices and systems. For example, certain embodiments relate to vessel sealing end effector devices, while other embodiments relate to dual end effector components incorporated into or used with robotic and/or in vivo medical devices. The term "dual end effector" as used herein shall mean an operational component having two or more interchangeable end effectors.

It is understood that the various embodiments of end effector devices or components disclosed herein can be incorporated into or used with any other known medical devices, systems and methods, including, but not limited to, robotic or in vivo devices as defined herein.

For example, the various embodiments disclosed herein can be incorporated into or used with any of the medical devices disclosed in copending U.S. application Ser. No. 11/932,441 (filed on Oct. 31, 2007 and entitled "Robot for Surgical Applications"), Ser. No. 11/695,944 (filed on Apr. 3, 2007 and entitled "Robot for Surgical Applications"), Ser. No. 11/947,097 (filed on Nov. 27, 2007 and entitled "Robotic Devices with Agent Delivery Components and Related Methods"), Ser. No. 11/932,516 (filed on Oct. 31, 2007 and entitled "Robot for Surgical Applications"), Ser. No. 11/766,683 (filed on Jun. 21, 2007 and entitled "Magnetically Coupleable Robotic Devices and Related Methods"), Ser. No. 11/766,720 (filed on Jun. 21, 2007 and entitled "Magnetically Coupleable Surgical Robotic Devices and Related Methods"), Ser. No. 11/966,741 (filed on Dec. 28, 2007 and entitled "Methods, Systems, and Devices for Surgical Visualization and Device Manipulation"), Ser. No. 12/171,413 (filed on Jul. 11, 2008 and entitled "Methods and Systems of Actuation in Robotic Devices"), Ser. No. 12/192,663 (filed on Aug. 15, 2008 and entitled "Medical Inflation, Attachment, and Delivery Devices and Related Methods"), Ser. No. 12/192,779 (filed Aug. 15, 2008 and entitled "Modular and Cooperative Medical Devices and Related Systems"), Ser. No. 12/324,364 (filed Nov. 26, 2008 and entitled "Multifunctional Operational Component for Robotic Devices"), 61/030,588 (filed on Feb. 22, 2008 and entitled Medical Devices having a Positionable Camera), Ser. No. 12/971,917 (filed on Dec. 17, 2010 and entitled "Modular and Cooperative Medical Devices and Related Systems and Methods"), 61/506,384 (filed on Jul. 11, 2011 and entitled "Robotic Surgical Devices, Systems, and Related Methods"), 61/542,543 (filed on Oct. 3, 2011 and entitled "Robotic Surgical Devices, Systems, and Related Methods"), 61/584,947 (filed on Jan. 10, 2012 and entitled "Methods, Systems, and Devices, for Surgical Access and Insertion"), and 61/640,879 (filed on May 1, 2012 and entitled "Single Site Robotic Device and Related Systems and Methods"), all of which are hereby incorporated herein by reference in their entireties.

In accordance with certain exemplary embodiments, any of the various embodiments disclosed herein can be incorporated into or used with a natural orifice translumenal endoscopic surgical device, such as a NOTES device. Those skilled in the art will appreciate and understand that various combinations of features are available including the features disclosed herein together with features known in the art.

Certain device implementations disclosed in the applications listed above can be positioned within a body cavity of a patient, including certain devices that can be positioned against or substantially adjacent to an interior cavity wall, and related systems. An "in vivo device" as used herein means any device that can be positioned, operated, or controlled at least in part by a user while being positioned within a body cavity of a patient, including any device that is positioned substantially against or adjacent to a wall of a body cavity of a patient, further including any such device that is internally actuated (having no external source of motive force), and additionally including any device that may be used laparoscopically or endoscopically during a surgical procedure. As used herein, the terms "robot," and "robotic device" shall refer to any device that can perform a task either automatically or in response to a command.

Further, the various end effector embodiments could be incorporated into various robotic medical device systems that are actuated externally, such as those available from Apollo Endosurgery, Inc., Hansen Medical, Inc., Intuitive Surgical, Inc., and other similar systems, such as any of the devices disclosed in the applications that are incorporated herein elsewhere in this application.

Figure 1B:
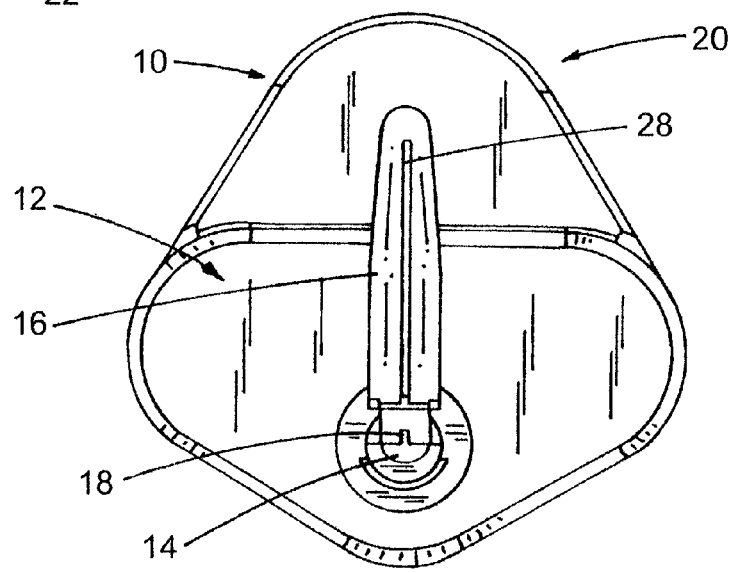
FIG. 1B is a front view of a vessel sealing device, according to one embodiment.
Figure 1C:
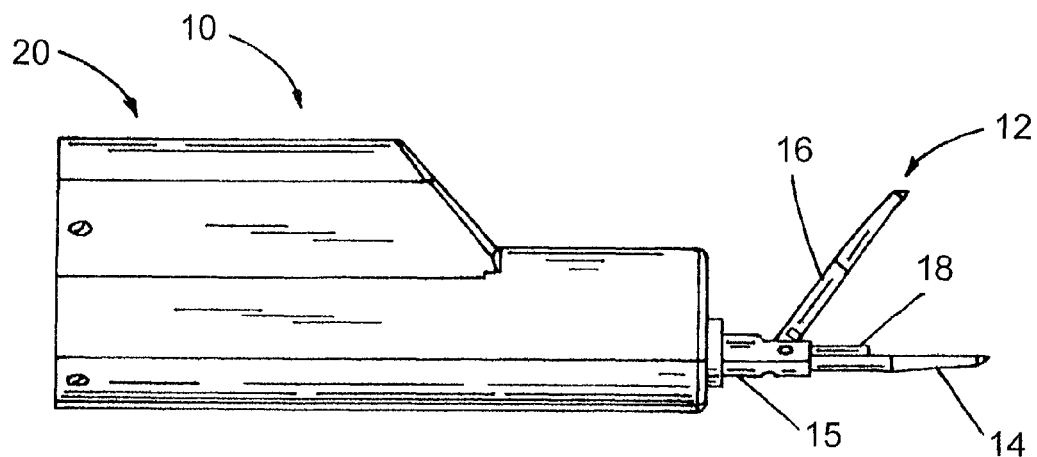
FIG. 1C is a side view of a vessel sealing device, according to one embodiment.

Certain embodiments disclosed herein relate to end effector devices for use in sealing vessels, including certain embodiments used in combination with any of the various procedural device embodiments described above. One such embodiment is a cautery device. FIGS. 1A-1C depict one embodiment of a cautery device 10 having a proximal end 30 and a distal end 40. In the cautery device 10 depicted in FIGS. 1A-1C, the device 10 includes a body 20 with a bipolar cautery component 12 at the distal end 40.

Known minimally-invasive in vivo cautery devices use a monopolar hook cautery component. In contrast, the embodiments disclosed herein provide a different device that cauterizes and cuts vessels with more precision and with reduced damage to the surrounding tissue.

As best shown in FIGS. 1A-1C, the bipolar cautery component 12, also termed a "cautery end effector" herein, includes a stationary jaw component 14, a mobile jaw component 16 for clasping and cauterizing a vessel (e.g., a vein or artery), and a cutting component 18 for cutting the cauterized vessel, thus providing a three function end effector 12. The stationary jaw component 14 and mobile jaw component 16 are structured like a pair of jaws, with the stationary jaw component 14 being configured to remain stationary during the cautery process, providing a substantially rigid and stable base to support a vessel. The mobile jaw component 16 is configured such that it can move in a jaw-like fashion in relation to the stationary jaw component 14 such that the mobile jaw component 16 can ultimately make contact with the vessel positioned between the stationary jaw component 14 and the mobile jaw component 16 to clasp the vessel between the jaws 14, 16.

Figure 6:
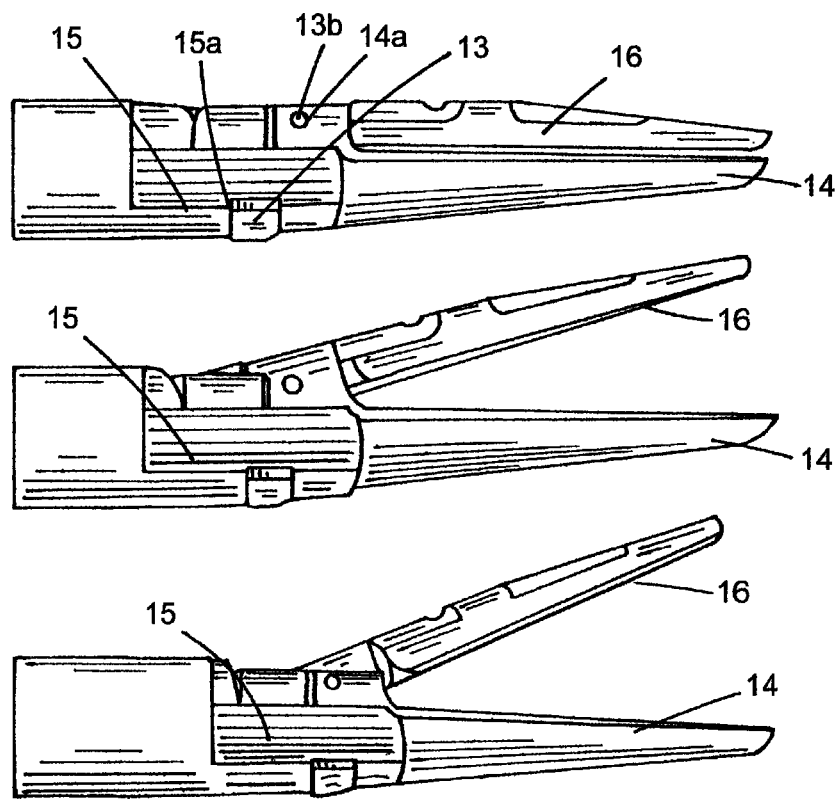
FIG. 6 is a view of a mobile jaw for a vessel sealing device in the closed position (top), partially open position (middle), and fully open position (bottom), according to one embodiment.
Figure 7:
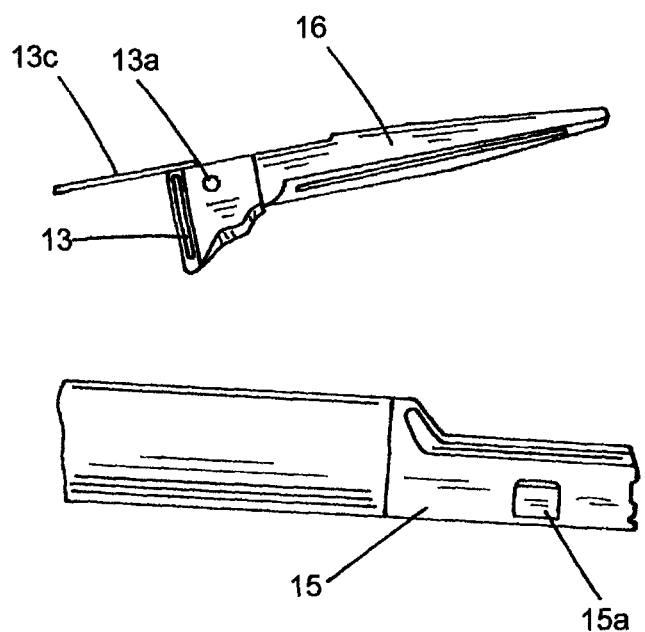
FIG. 7 is a side view of a mobile jaw (top) and an outer shell (bottom) for a vessel sealing device, according to one embodiment.

As best shown in FIGS. 6 and 7, according to one embodiment, the mobile jaw 16 additionally includes a pivot component 13 that that projects laterally from the proximal end of mobile jaw 16 and includes a receptacle 13a for receiving a pin 13b. The pivot component 13 is generally peg- or wedge-shaped to fit through an opening in outer shell 15 and facilitates movement of mobile jaw 16 as described herein below. Stationary jaw 14 includes an opening 14a configured to align with receptacle 13 and receive pin 13b.

Returning to FIGS. 1A-1C, each of the fixed jaw component 14 and mobile jaw component 16 is connected to a source of electrical current (not shown) such that the jaws 14, 16 function as bipolar electrodes, with one jaw functioning as a cathode and one jaw functioning as an anode when an electric current is applied. In certain implementations, the source for electrical current is a generator (not shown) that provides current separately from electricity powering the motors. In some embodiments, the generator is located outside of device 10 as a separate component. In use, the electricity flowing through the jaws 14, 16 creates heat which cauterizes a vessel clasped between the jaws 14, 16. In some embodiments, the current is applied discretely by the operator by, for example, pressing a button or flipping a switch on the generator.

Figure 4:
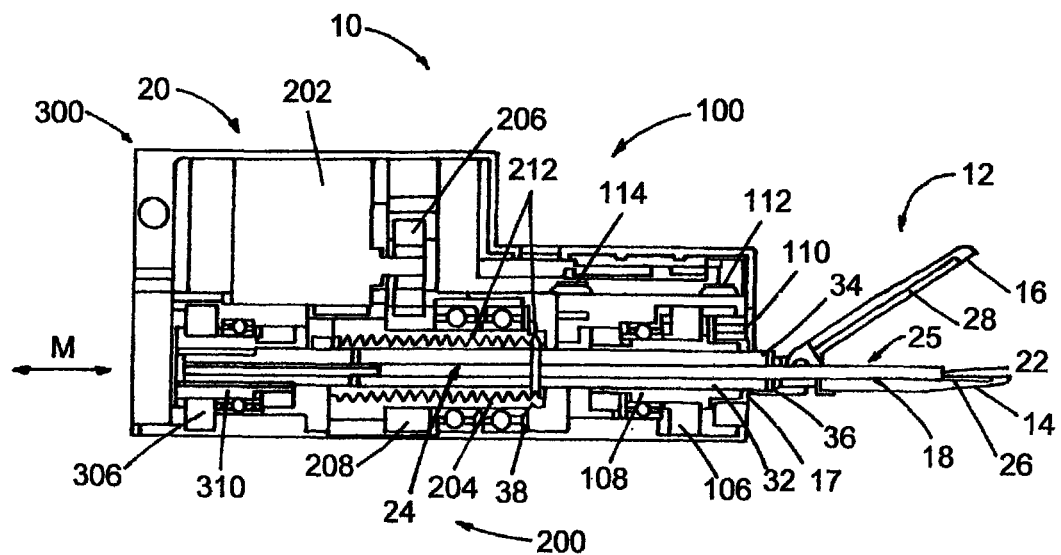
FIG. 4 is a side view of a vessel sealing device longitudinally sectioned to show inner components, according to one embodiment.
Figure 5:
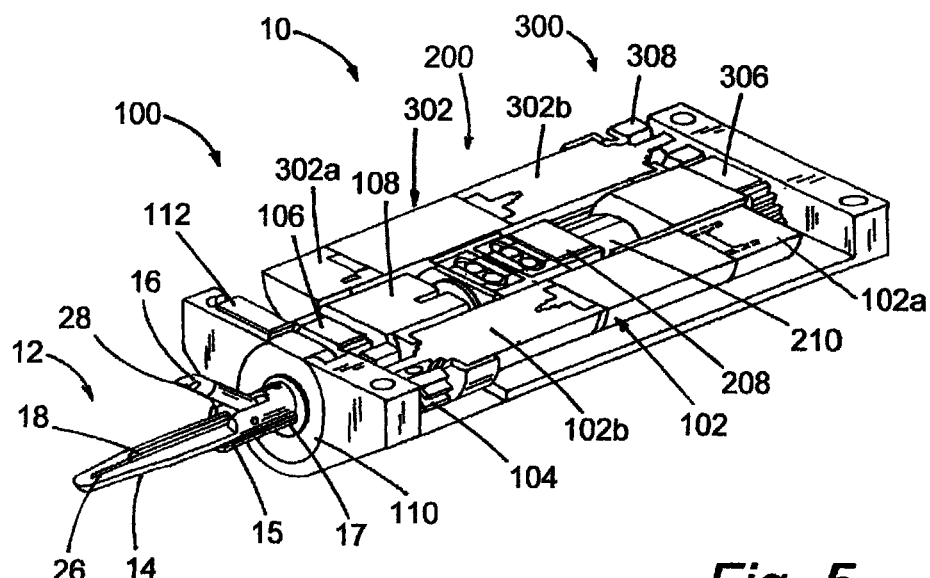
FIG. 5 is a perspective view of a vessel sealing device laterally sectioned to show inner components, according to one embodiment.

As best shown in FIG. 4, the stationary jaw 14 of the bipolar cautery end effector 12 is attached to a shaft 32 that extends proximally from the stationary jaw 14 and is disposed within the body 20. The cutting component 18 is positioned between the jaws 14, 16 (as shown in FIGS. 1A-1C and 4) and extends through the shaft 32. The shaft 32 has a slot 39 cut into either or both the top 34 or bottom 36 sides of the shaft 32 and extending longitudinally along part of the length of the shaft 32 to accommodate a pin 38 (as shown in FIG. 4) that extends through the slot 39 and attaches to or extends through the cutting component 18 such that the pin is coupled to the cutting component. As such, the pin 38 and cutting component 18 can slide together along the slot 39 from a generally proximal first position to a more distal second position along with the cutting component 18. In some embodiments as best shown in FIG. 5, one or both of the stationary jaw 14 and mobile jaw 16 have a channel 26, 28 within which the cutting component 18 moves from the first position to the second position.

In the embodiment illustrated in FIG. 4, the cutting component 18 is substantially elongate and has a proximal end 24 and a distal end 25. The cutting component 18 includes a cutting surface 22 at the distal end 25 such that when the cutting component 18 is moved from the generally proximal first position to the more distal second position, the cauterized vessel enclosed between the jaws 14, 16 of the cautery device 10 is cut at the point of cautery.

Figure 2:
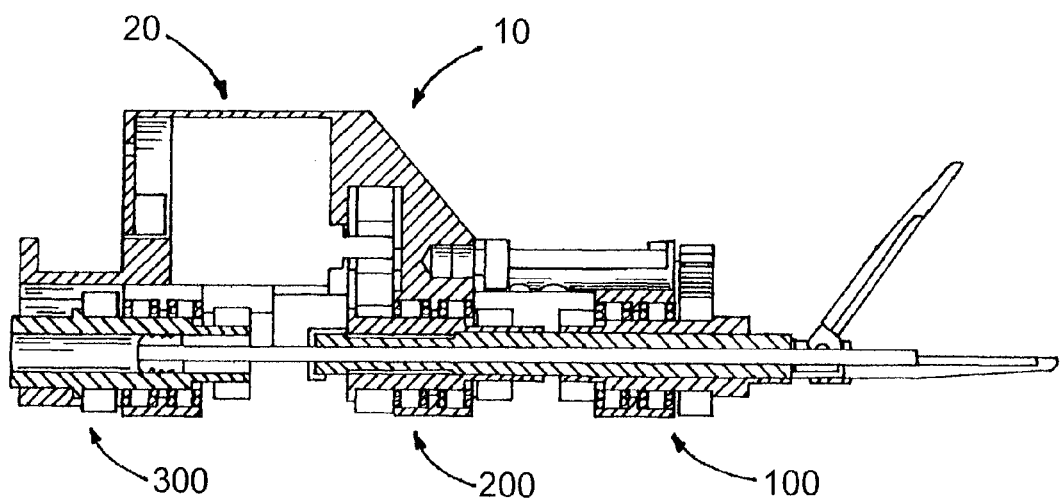
FIG. 2 is a side view of a vessel sealing device longitudinally sectioned to show component staging, according to one embodiment.

For ease of description and understanding, the cautery device 10 as described herein has three sections 100, 200, 300, as illustrated in FIG. 2. In this embodiment, each section generally defines a plurality of components configured to control a function of the cautery device 10 within the body 20. As such, the first section 100 controls the application of the electrical current to the jaws 14, 16 as described above and rotation of the bipolar cautery end effector 12. The second section 200 controls positioning of the cutting component 18. Finally, the third section 300 controls opening and closing of the jaws 14, 16 of the bipolar cautery end effector 12. It is to be understood that while the illustrated embodiments utilize three sections, this identification and division of sections is provided solely for ease of description and understanding. It is also understood that the sections may be combined or split into more or fewer sections. For example, the first section 100 may be split into two sections separately controlling electrical current and end effector rotation.

According to some embodiments, the sections are configured and positioned such that the first section 100 is proximal to the bipolar cautery end effector 12, while the third section 300 is located closest to the proximal end 30 of the device 10, with the second section 200 being located between the first and third sections 100, 300. In some embodiments, the sections are configured and positioned such that the shape of the cautery device 10 becomes more slender toward the distal end. It is to be understood, however, that the sections may be configured or positioned in any manner suitable for proper function of the device, and may include any modifications that provide functional, aesthetic, and/or manufacturing advantages. Such advantages include, without limitation, visibility of the bipolar cautery end effector 12, size reduction, reduced materials costs, and the like.

Power for the various functions of the device 10 as described herein is provided by the motors 102, 202, 302, as best shown in FIGS. 4 and 5. Electrical current for the motors 102, 202, 302 is provided by an electrical source (not shown). According to one implementation, the electrical source is positioned externally in relation to the device 10. Alternatively, the electrical source can be positioned within the device. In some embodiments, the source of electricity for motors 102, 202, 302 also includes a control device (not shown) that includes components for controlling the motors 102, 202, 302 and/or sensing the status (e.g., position) of motors 102, 202, 302. For example, the control device could be an external control device configured to be manipulated by a user. In some embodiments, the source of electric current for motors 102, 202, 302 is separate from the control device. In other embodiments, each motor 102, 202, 302, is controlled and/or powered separately from one another. In some embodiments, the electricity for motors 102, 202, 302 is provided by the same electricity source as the current provided to jaws 14, 16.

As best shown in FIG. 5, one or more of motors 102, 202, 302 have an encoder, e.g., 102a, 302a, (not shown for motor 202), which is connected to the control device for receiving control instructions from the control device and providing data about the status of motors 102, 202, 302 to the control device. In some embodiments, one or more motors 102, 202, 302 also have a gear head, e.g., 102b, 302b, (not shown for motor 202). The gear heads 102b, 302b, (not shown for motor 202) can be fixed or, in some embodiments, removable and interchangeable to provide multiple gear ratios.

In accordance with one implementation, due to the electrical nature of the bipolar cautery end effector 12, the drivetrain—including the first 100, second 200, and third 300 sections of the device—is electrically isolated from the motors 102, 202, 302 through the use of non-conductive gears driven by the motors 102, 202, 302. In one embodiment, the non-conductive gears are made of nylon. Alternatively, the gears can be made of any known non-conductive material that can be used in gears. The non-conductive gears inhibit electrical current from flowing through the drive train to the jaws 14, 16 and producing electrical interference that affects communication between the motors 102, 202, 302 and control device. In some embodiments, both conductive and non-conductive gears are used. For example, in one implementation, as best shown in FIGS. 4 and 5, gears 106, 208, 306 are made of non-conductive material, while gears 104, 206, 308 are made of a conductive material. In accordance with another implementation, the effect of electrical interference can be reduced through the use of interference-reducing software and/or components in the control device or encoder 102a, 302a instead of, or in addition to, the use of non-conductive gears.

As best shown in FIGS. 3A and 5, the first section 100 of the cautery device 10 includes a first section motor 102 that is operatively coupled to the bipolar cautery end effector 12 to control rotation of the bipolar cautery end effector 12. In some embodiments, the first section motor 102 is directly coupled to the bipolar cautery end effector 12 or can be indirectly coupled to the bipolar cautery end effector 12 by one or more coupling means. For example, in the embodiment illustrated in FIGS. 3A and 3B, the first section motor 102 is coupled to the bipolar cautery end effector 12 by a first gear 104 and a second gear 106, the second gear 106 being attached to the shaft 32 of the bipolar cautery end effector 12 via metal coupler 108, as best shown in FIG. 5, such that rotational movement produced by the first section motor 102 is transferred to rotational movement of the bipolar cautery end effector 12 around axis A depicted in FIG. 3A. In some embodiments, metal coupler 108 is coupled to the bipolar cautery end effector 12 via an outer shell 15. As best shown in FIGS. 6 and 7, outer shell 15 projects distally from the metal coupler 108 and includes an opening 15a through which pivot component 13 on mobile jaw 16 projects and translates rotational movement of coupler 108 to shaft 32.

Second gear 106 can be fixed to the metal coupler 108 using, for example, an adhesive (e.g., UV cure glue). In some embodiments, the second gear 106 and the metal coupler 108 are configured such that the shape of each component prevents the second gear 106 from moving relative to the metal coupler 108 (i.e., non-circular geometry). For example, the metal coupler 108 can be generally square-shaped to fit into a generally square-shaped hole in the second gear 106.

Returning to FIG. 4, the first section 100 additionally includes components for applying electrical current to the jaws 14, 16. In this embodiment, the first section 100 includes an electrical connection 110 for the mobile jaw 16. The electrical connection 110 is configured to allow sliding contact to a first slip ring 112, which is connected to a source of electrical current (not shown) either directly or indirectly. Slip ring 112 is generally U-shaped or C-shaped such that it maintains contact with electrical connection 110 when electrical connection 110 rotates with shaft 36. The use of slip ring 112 rather than a wire to provide electrical connection to connection 110 prevents twisting of wires about the drive train as connection 110 rotates. Mobile jaw 16 is electrically connected to connection 110 via a conductor, such as wire 13c shown in FIG. 7 or other appropriate conductor. Electrical connection 110 is electrically isolated from stationary jaw 14 by the inclusion of a non-conductive (e.g., plastic) ring 17 between the connection 110 and the stationary jaw 14. The first section also includes a second slip ring 114 associated with the stationary jaw 14, that functions similarly to the first slip ring 112 by maintaining electrical contact with shaft 36 during rotation. The use of slip rings 112, 114 to separately provide current to jaws 16, 14, respectively, allows one jaw to function as a cathode and one jaw to function as an anode when an electric current is applied. In some embodiments, it may be desirable to include additional components or modifications to limit or focus electrical communication between jaws 14, 16.

The second section 200 in the embodiment shown in FIG. 4 includes a second section motor 202 that is operatively coupled to the cutting component 18 to control movement of the cutting component 18 from a first position to a second position along line of movement M. The second section motor 202 is coupled to a threaded collar 204 either directly or indirectly via a coupling means. In the embodiment illustrated in FIG. 4, the coupling means for coupling the second section motor 202 to the threaded collar 204 includes a first gear 206 connecting the second section motor 202 to a second gear 208, the second gear 208 being attached to the threaded collar 204 using, for example, an adhesive (e.g., UV cure glue) or non-circular geometry, as described above. An end of the pin 38 attached to or extending through the cutting component 18 is seated in a thread 212 of the threaded collar 204 such that rotational movement produced by the second section motor 202 is translated to lateral movement of the pin 38 along M and thereby the cutting component 18. The second section is configured such that the movement of the cutting component 18 along M is a distance ranging from about 0.5 to about 1.0 inches in order to cut a vessel clasped between jaws 14, 16. Alternatively, the distance ranges from about 0.7 inches to about 1.0 inches. However, the distance can be adjusted as appropriate for the vessel size and specific configuration of the cautery device 10. In one embodiment, the pivot component 13 of mobile jaw 16 includes an opening through which the cutting component 18 passes when moved. When not being used to cut a vessel, the cutting component 18 is retracted to a position proximal to the jaws 14, 16 such that the mobile jaw 16 may be opened or closed.

The third section 300 illustrated in FIGS. 4 and 5 includes a third section motor 302 that is operatively coupled to mobile jaw 16 to control opening and closing of the jaws 14, 16. In some embodiments, the third section motor 302 is directly coupled to shaft 32 or can be indirectly coupled to shaft 32 by one or more coupling means. For example, in the embodiment illustrated in FIGS. 4 and 5, the third section motor 302 is coupled to the shaft 32 by a first gear 308 and a second gear 306, the second gear 306 being attached to collar 310 using, for example, an adhesive (e.g., UV cure glue) or non-circular geometry. In some embodiments, the shaft 32 and collar 310 are threaded such that rotation produced by motor 302 is translated to lateral movement of the shaft 32 along M and thereby the jaws 14, 16 relative to outer shell 15. As best seen in FIG. 6, opening 15a restricts lateral movement of pivot component 13 of mobile jaw 16 along M relative to outer shell 15 such that lateral translation of shaft 32 along M causes mobile jaw 16 to open or close by pivoting around pin 13b via the pivot component 13 at opening 15a.

In an alternative embodiment, stationary jaw 14 can be replaced with a second mobile jaw. In this embodiment, the second mobile jaw is pivotably attached to shaft 32 and includes a pivot component similar to pivot component 13. In this embodiment, outer shell 15 is configured to include a second opening similar to opening 15a that restricts lateral movement of the pivot component of the second mobile jaw such that the second mobile jaw is opened and closed via translation of shaft 32 along M in a manner similar to mobile jaw 16.

The third section 300 can further include a means for detecting the thickness of a vessel clasped between the jaws 14, 16. Vessel thickness can be calculated, for example, based on the amount of lateral translation of shaft 32 along M required to close mobile jaw 16 or the position of mobile jaw 16 relative to stationary jaw 14. In some embodiments, the position of mobile jaw 16 relative to stationary jaw 14 is determined for example, by measuring electrical impedance between jaws 14, 16.

As discussed above, the cautery device embodiments disclosed herein can be utilized in any type of medical device, including those devices in which a compact or smaller size is desirable, such as devices for procedures to be performed within a patient. In order to achieve a cautery device with appropriate dimensions for such use, the dimensions of components disclosed herein can be adjusted to control the overall size of the device. For example, in one implementation, the motors 102, 202, 302 can range in size from about 8 mm to about 15 mm, while the overall length of the body is kept under about 3 inches. In some embodiments, the overall length of the cautery component is kept under about 1.5 inches. In some embodiments, the height and/or width is kept under 2 inches. Alternatively, other dimensions can be used depending on size, weight, and/or visibility requirements.

In use, the cautery device 20 is positioned next to the target vessel using a complementary system or device as described elsewhere such as an articulating robotic arm. Next, the cautery device 20 operates in the following manner to cauterize the vessel. The first section motor 102 rotates the cautery end effector 12 to position the jaws 14, 16 in an alignment with the vessel such that the jaws may enclose the vessel. The third section motor 302 actuates the mobile jaw 16 to open and the cautery end effector 12 is positioned such that the vessel is located between the jaws 14, 16. The third section motor 302 then actuates the mobile jaw 16 to close with the vessel disposed between the jaws 14, 16 and the source of electrical current (not shown) applies an electric current to the vessel via the jaws 14, 16, thereby cauterizing it. The second section motor 202 drives the cutting component 18 toward the distal end of the cautery device 20 and thus pushes the cutting surface 22 through the vessel enclosed in the jaws 14, 16, thereby cutting the vessel.

FIGS. 8A-22 depict a dual end effector operational component 410 that can be incorporated into any one of a variety of medical devices as described above. In this embodiment, the dual end effector operational component 410 is positioned on the end of a robotic arm 412. It is further understood that the robotic arm 412 can be part of any robotic medical device, such as an in vivo device. As best shown in FIGS. 8A-10B, the arm 412 has two arm segments, including a first arm segment (or "upper arm") 412A and a second arm segment (or "forearm") 412B. The first arm segment 412A is rotatably coupled with a torso motor housing 414 via a joint or hinge (not shown). The torso motor housing 414 houses a motor and actuation mechanism (not shown) to provide rotation of the first arm segment 412A relative to the torso motor housing 414. Further, the first arm segment 412A is rotatably coupled to the second arm segment 412B at joint 416A, while the second arm segment 412B is rotatably coupled to the dual end effector operational component 410 at joint 416B.

In one embodiment, the dual end effector operational component 410 has an actuator housing 418 and an end effector housing 420. The end effector housing 420 has two end effector elements 422, 424. In the embodiment depicted in FIGS. 8A-10B, one end effector element is a cautery component 422 and the second end effector element is a grasper 424. Alternatively, the end effector elements on the dual end effector operational component 410 can be any known end effectors for use with medical devices, such as, for example, forceps, needle drivers, scissors, Ligasure™, or knife components, to list a few.

Figure 8A:
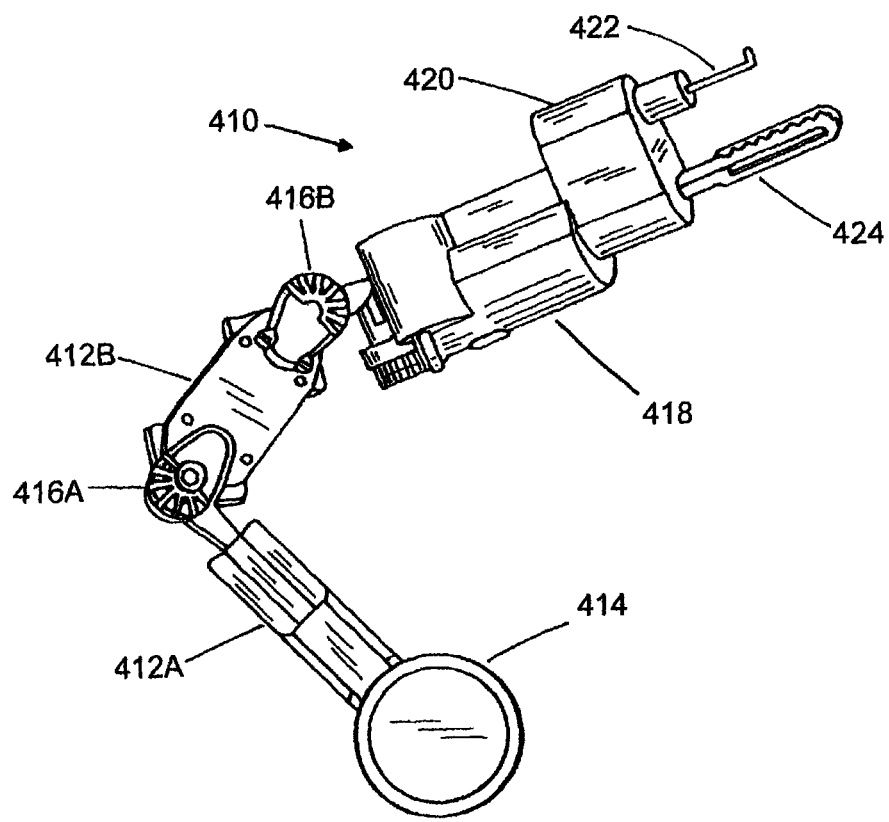
FIG. 8A is a perspective top view of a medical device with a dual end effector component in a first orientation, according to one embodiment.
Figure 8B:
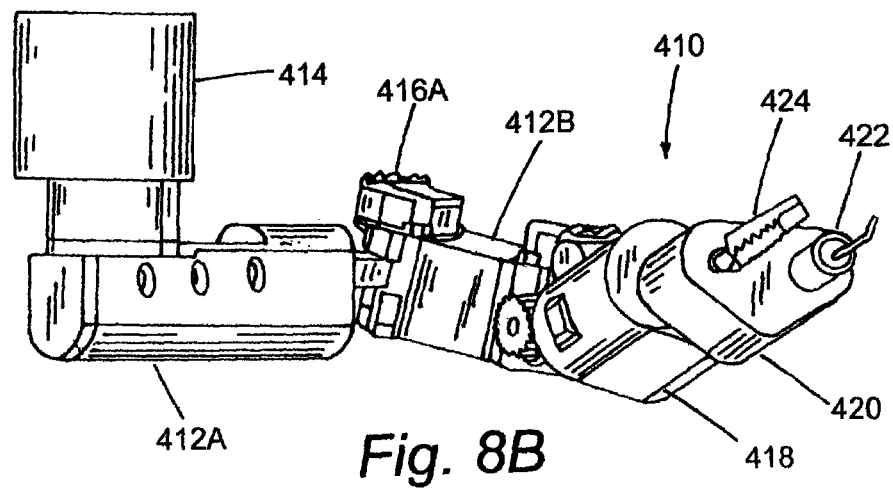
FIG. 8B is a perspective side view of the device and component of FIG. 8A in a first orientation.

As best shown in FIGS. 8A and 8B, in one embodiment, although both end effector elements 422, 424 remain operable, the end effector housing 420 is oriented so that the grasper 424 is accessible to the subject tissue and can perform a medical procedure.

Figure 9A:
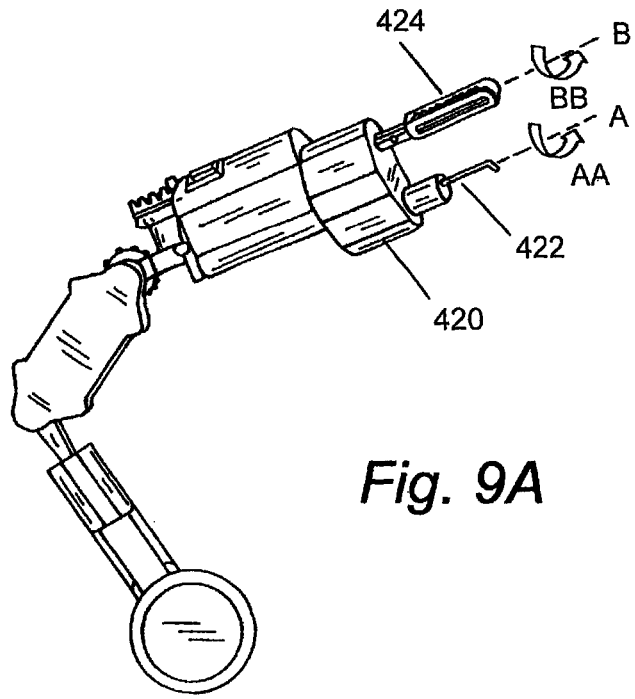
FIG. 9A is a perspective top view of the device and component of FIG. 8A in a second orientation.
Figure 9B:
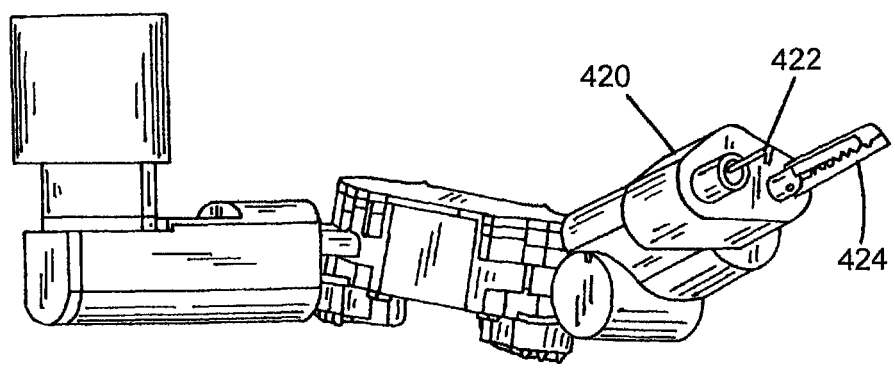
FIG. 9B is a perspective side view of the device and component of FIG. 8A in a second orientation.

As best shown in FIGS. 9A and 9B, in another embodiment, although both end effector elements 422, 424 remain operable, the end effector housing 420 is oriented so that the cautery component 422 is accessible to the subject tissue and can perform a medical procedure.

In one embodiment, both end effector elements 422, 424 can rotate in relation to the end effector housing 420. More specifically, as best shown in FIG. 9A, the cautery component 422 is rotatable relative to the end effector housing 420 as shown by arrow AA around an axis indicated by line A. Further, the grasper 424 is rotatable relative to the end effector housing 420 as shown by arrow BB around an axis indicated by line B. According to one embodiment, the grasper 424 is also configured to move between an open configuration and a closed configuration (not shown). In an alternative embodiment (not shown), both end effector elements 422, 424 can rotate relative to the end effector housing 420 and also can be configured to move between an open configuration and a closed configuration, depending on the type of end effectors. In another alternative embodiment, the two end effectors can be operably coupled to each other such that both end effectors can be configured to move between open and closed positions.

Figure 10A:
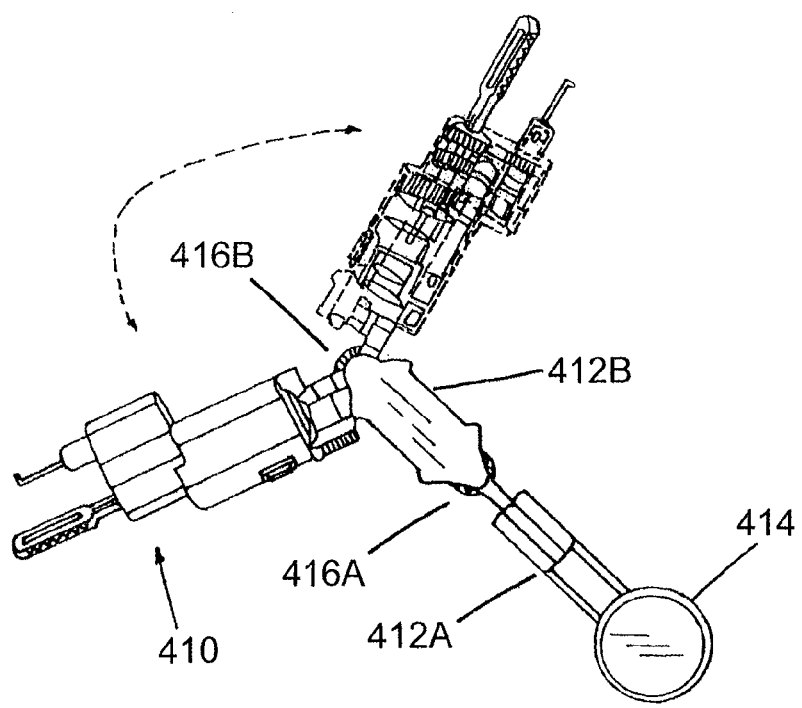
FIGS. 10A and 10B are schematic representations of the bi-directional range of motion of the component of FIG. 8A.

As best shown in FIG. 10A, in one embodiment, the dual end effector operational component 410 can be rotated relative to the second arm segment 412B via the joint 416B and an actuation motor and gear system (not shown) contained within the second arm segment 412B.

Figure 10B:
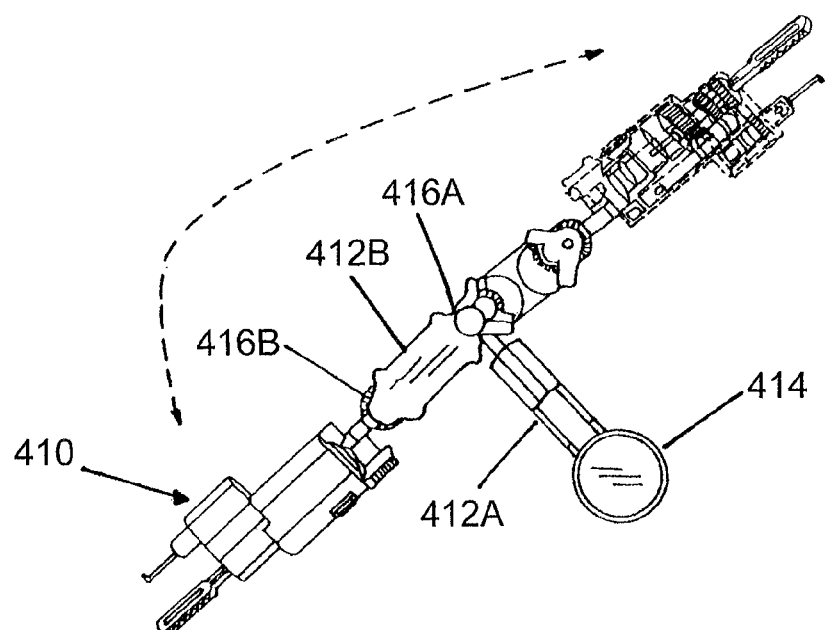
Figure 11A:
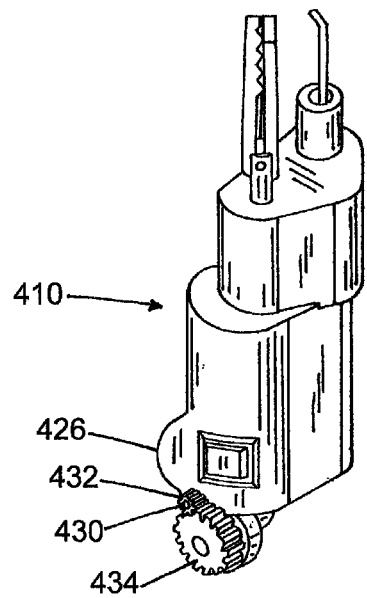
FIGS. 11A and 11B are perspective isometric views of the component of FIG. 8A.
Figure 11B:
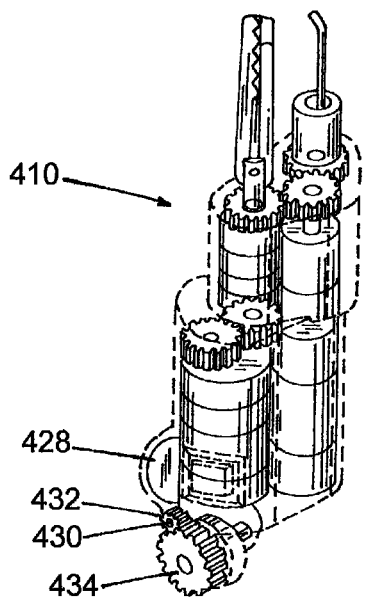
Figure 12A:
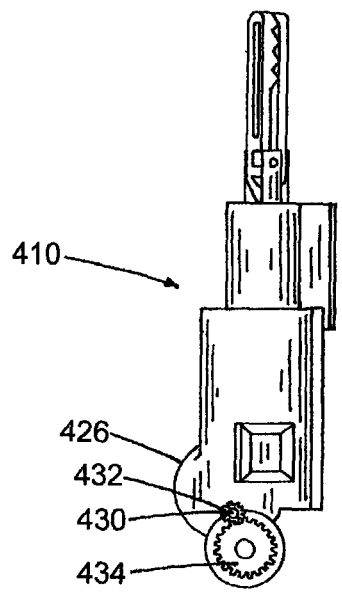
FIGS. 12A and 12B are perspective side views of the component of FIG. 8A.
Figure 12B:
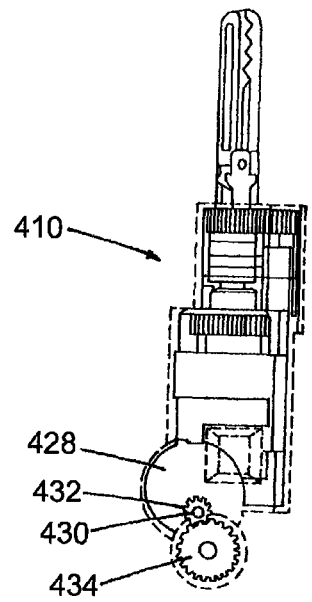

As best shown in FIG. 10B, in one embodiment, the dual end effector operational component 410 and the second arm segment 412B can be rotated relative to the first arm segment 412A via the joint 416A and an actuation motor and gear system (not shown) within the first arm segment 412A.

As best shown in FIGS. 11A-12B, within the dual end effector 410, the forearm gear housing 426 contains an actuation motor 428 that is rigidly coupled to a driveshaft 430. The driveshaft 430 is rigidly coupled to a rotational motor spur gear 432. The rotational motor spur gear 432 is rotatably coupled to a rotational gear 434 that is rigidly coupled to the second arm segment (such as, for example, the second arm segment 412B as shown in FIGS. 8A-10B). Actuation of the actuation motor 428 causes rotation of the driveshaft 430 and the rotational motor spur gear 432. Rotation of the rotational motor spur gear 432 causes rotation of the dual end effector operational component 410 relative to the second arm segment (such as second arm segment 412B).

Figure 13A:
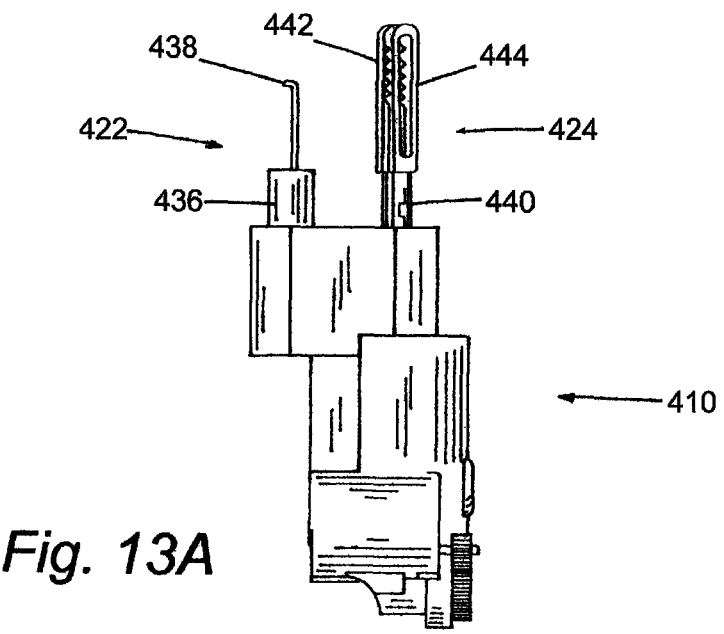
FIGS. 13A and 13B are perspective front views of the component of FIG. 8A.
Figure 13B:
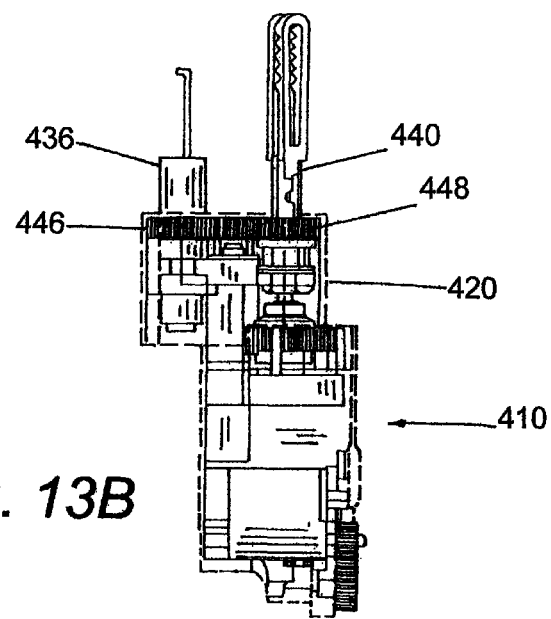

As best shown in FIGS. 13A and 13B, in one embodiment, the cautery component 422 has a proximal cautery housing 436 rigidly attached to a distal cautery tip 438. In one embodiment, the wire (not shown) supplying electricity to the cautery tip 438 is enclosed in the cautery housing 436. The wire runs proximally through the dual end effector operational component 410 and is coupled at a proximal end of the wire to a power source such as a standard electrocautery generator (not shown). In another embodiment, the power source could be located within the dual end effector operational component 410. According to the implementation as shown, the grasper 424 has a proximal grasper housing 440 coupled to two grasping elements 442, 444.

As best shown in FIG. 13B, in one embodiment, the cautery housing 436 is rigidly coupled to a cautery rotational gear 446 within the end effector housing 420. Further, the grasper housing 440 is rigidly connected to the grasper rotational spur gear 448 within the end effector housing 420.

Figure 14:
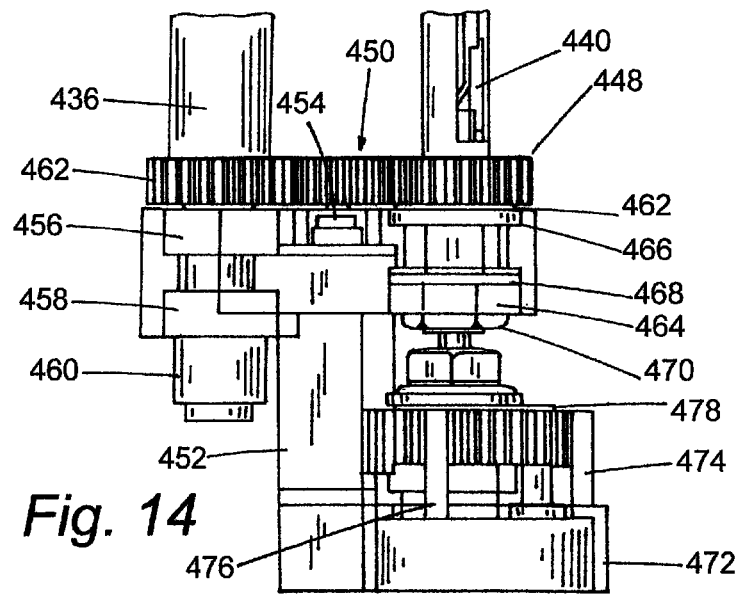
FIG. 14 is a perspective front view of the component of FIG. 8A.

As best shown in FIG. 14, the cautery rotational gear 446 is rotatably coupled with a rotational motor spur gear 450. The rotational motor spur gear 450 is rotatably actuated by a rotational motor 452 and a rotational motor gearhead 454 coupled to the motor 452. Actuation of the rotational motor 452 and rotational motor gearhead 454 causes rotation of the rotational motor spur gear 450, and thus the cautery rotational gear 446 and the cautery housing 436. The cautery housing 436 is further coupled to two bearing elements 456, 458 proximal to the cautery rotational gear 446: a distal bearing 456 and a proximal bearing 458, both of which support the cautery housing 436 and reduce rotational friction thereof. The cautery housing 436 and proximal bearing 458 are further coupled to a cautery housing preload nut 460 that limits translation of the cautery housing 436 and provides a preload or clamping force for the two bearing elements 456, 458 to aid in reducing friction during rotation of the cautery housing 436 by holding the bearing elements 456, 458 in place during rotation.

In one embodiment, the grasper rotational spur gear 448 is rotatably coupled with the rotational motor spur gear 450. Actuation of the rotational motor 452 and rotational motor gearhead 454 causes rotation of the rotational motor spur gear 450, and thus causes rotation of the grasper rotational spur gear 448 and the grasper housing 440 simultaneously with rotation of the cautery housing 436.

In one embodiment, proximal to the grasper rotational spur gear 448, the grasper housing 440 is coupled to two beveled washer elements—a distal beveled washer element 462 and a proximal beveled washer element 464—that provide compliance for the grasper and prevent contact between moving parts during rotation of the grasper housing 440. The grasper housing 440 is further coupled to two bearing elements—a distal bearing 466 and a proximal bearing 468—that provide support for and reduce rotational friction of the grasper housing 440. The grasper housing 440 is further coupled to a distal hex preload nut 470 that limits translation of the grasper housing 440 and provides a preload or clamping force for the bearings 466, 468 to help reduce friction during rotation of the grasper housing 440 by holding the bearings 466, 468 in place during rotation.

In one embodiment, an actuation motor 472 is rigidly coupled to an actuation motor housing 474 by two actuation motor mounting bolts 476, 478. The actuation motor mounting bolts 476, 478 constrains the translation and rotation motion of the actuation motor 472 to the actuation motor housing 474.

Figure 15:
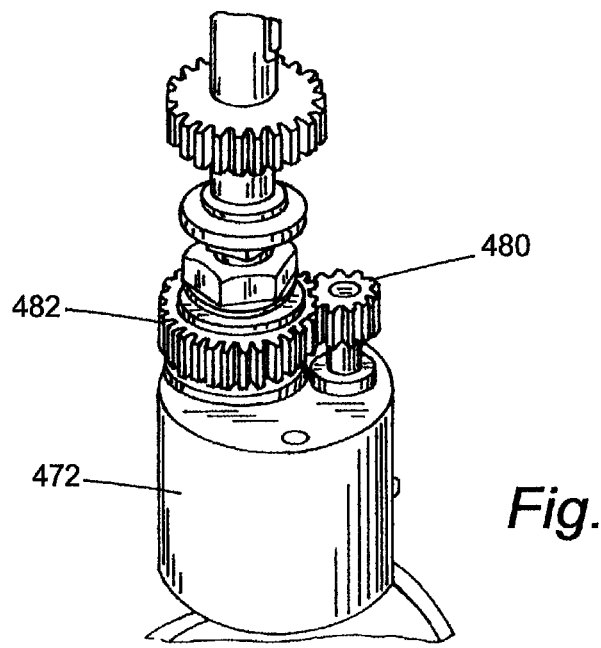
FIG. 15 is a perspective top view of the component of FIG. 8A.

As best shown in FIG. 15, in one embodiment, the actuation motor 472 is rigidly coupled to the actuation motor spur gear 480. Actuation of the actuation motor 472 causes rotation of the actuation motor spur gear 480 and this rotation is translated to the driveshaft housing spur gear 482.

Figure 16:
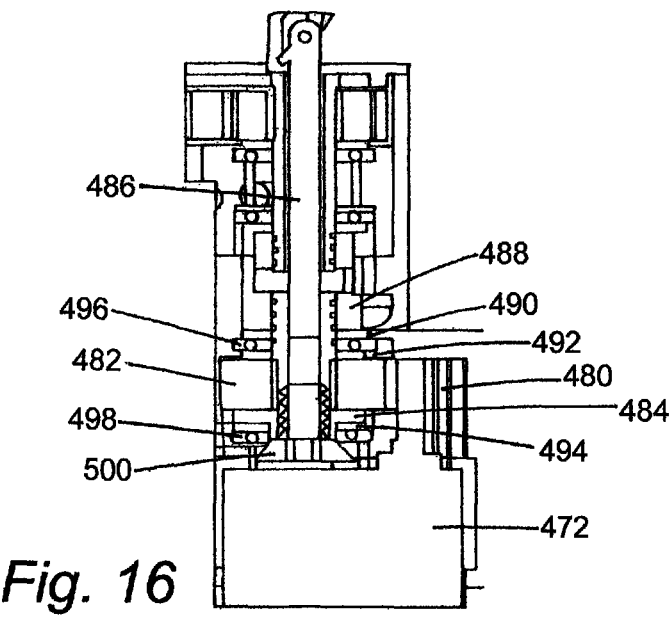
FIG. 16 is a perspective side view of the component of FIG. 8A.

As best shown in FIG. 16, the driveshaft housing spur gear 482 is rigidly coupled to the driveshaft housing 484 which is, in turn, rotatably coupled to the grasper driveshaft 486. Rotation of the driveshaft housing spur gear 482 via actuation of the actuation motor 472 and the actuation motor spur gear 480 therefore results in rotation of the driveshaft housing 484. Rotation of the driveshaft housing 484 in turn causes translation of the grasper driveshaft 486.

In one embodiment, rotation of the driveshaft housing 484 is aided by a proximal hex preload nut 488, several beveled washer elements 490, 492, 494 and bearing elements 496, 498. The driveshaft housing 484 is further rigidly coupled to a driveshaft housing screw 500 that constrains translation of the driveshaft housing 484 to the proximal bearing 498.

Figure 17:
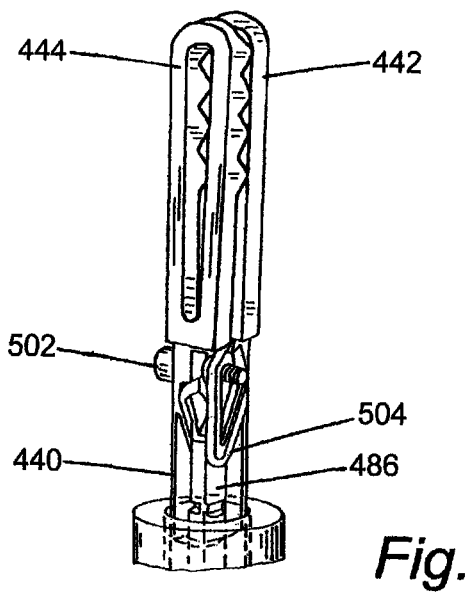
FIG. 17 is a perspective isometric view of the component of FIG. 8A.

As best shown in FIG. 17, a grasper rotational pin 502 is threaded through one side of the grasper housing 440, through a hole in each of the grasping elements 442, 444 and is rigidly coupled on the opposite side of the grasper housing 440. As the grasper driveshaft 486 is translated via rotation of the driveshaft housing 484 (as best shown in FIG. 16), a connector pin 504 that connects the grasper driveshaft 486 to the grasper elements 442, 444 slides up and down in the grooves of the grasper elements 442, 444. This translation in turn causes the grasper elements 442, 444 to open and close.

Figure 18:
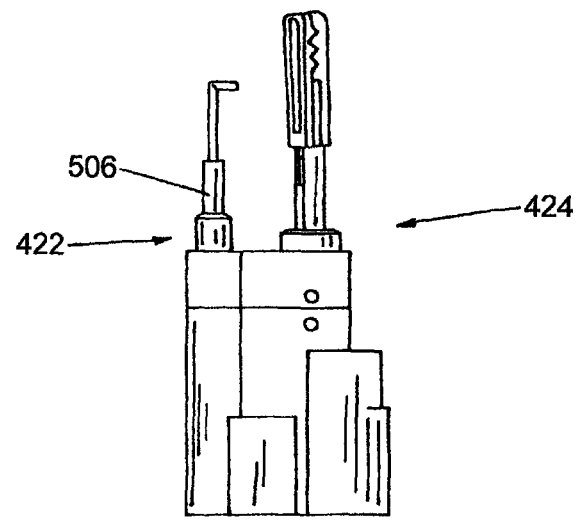
FIG. 18 is a perspective front view of the component of FIG. 8A.
Figure 19:
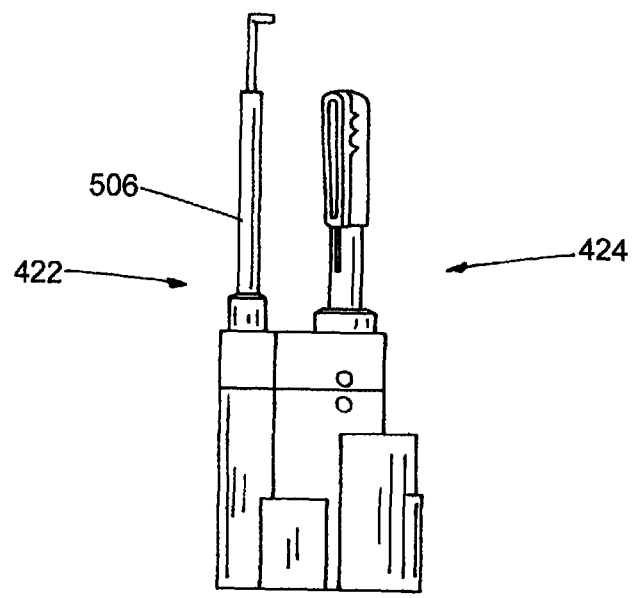
FIG. 19 is a perspective front view of the component of FIG. 8A.

As best shown in FIGS. 18 and 19, the cautery component 422 can extend and retract as necessary for operation and accessibility of the desired end effector element. As best shown in FIG. 18, the cautery component 422 can be retracted through retraction of the retractable cautery shaft 506 during operation of the grasper 424 so that unwanted contact with tissue by the cautery component 422 can be avoided. As best shown in FIG. 19, during operation of the cautery component 422, the cautery component 422 can be extended beyond the proximal tip of the grasper 424 by extension of the retractable cautery shaft 506.

Figure 20:
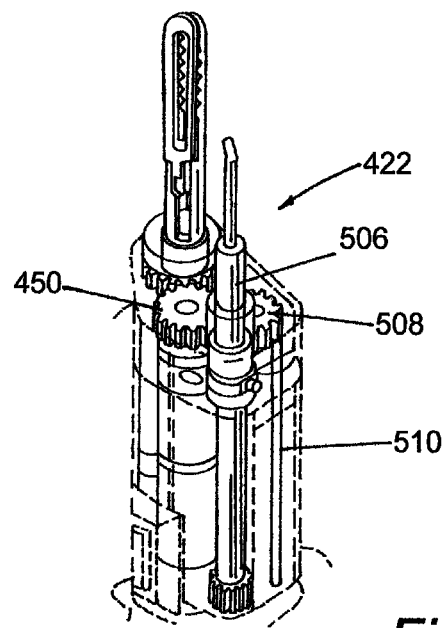
FIG. 20 is a perspective isometric view of the component of FIG. 8A.
Figure 21:
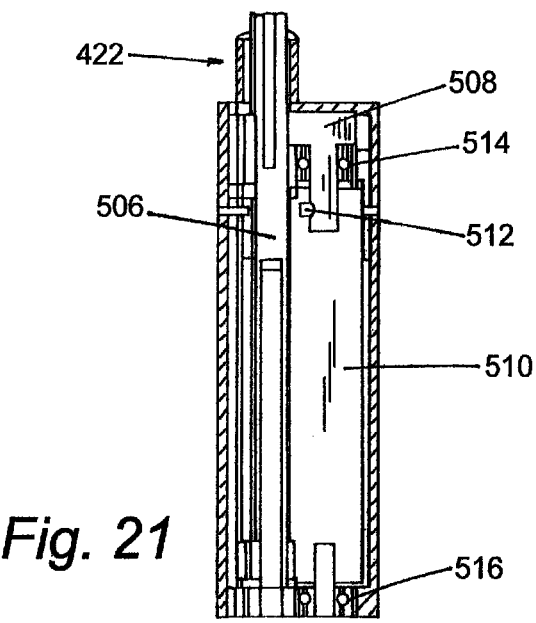
FIG. 21 is a perspective side view of the component of FIG. 8A.

As best shown in FIGS. 20 and 21, the cautery component 422 is extended and retracted through rotation of the rotational motor spur gear 450. The rotational motor spur gear 450 is rotatably coupled to the upper long cautery shaft 508. The upper long cautery shaft 508 is rigidly coupled to the lower long cautery shaft 510 via a set screw 512. The lower long cautery shaft 510 is supported by two bearing elements 514, 516. The lower long cautery shaft 510 is rotatably coupled to the retractable cautery shaft 506.

Figure 22:
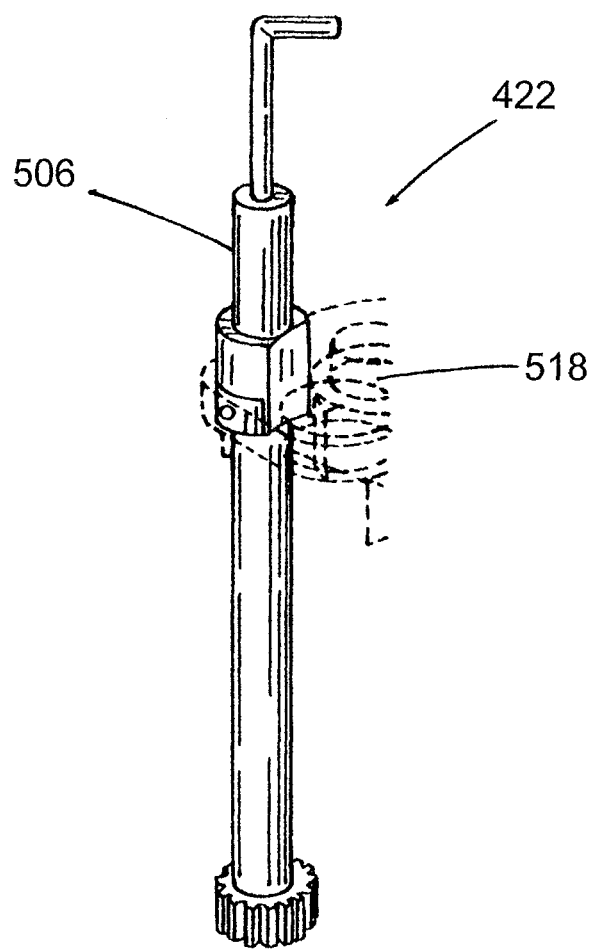
FIG. 22 is a perspective isometric view of the component of FIG. 8A.

As best shown in FIG. 22, rotation of the lower long cautery shaft 510 (depicted in FIGS. 20 and 21) causes the retractable cautery shaft 506 to retract or extend via external threading on the retractable cautery shaft 506 and internal threading on the threaded cautery energizing ring 518. The external threading of the retractable cautery shaft 506 causes the retractable cautery shaft 506 to translate up and down when the lower long cautery shaft 510 (depicted in FIGS. 20 and 21) is rotated. Power is supplied to the cautery component 422 via a wire (not shown) connected to the energizing ring 518.

As discussed above, the various embodiments disclosed herein relate to end effector devices that can be incorporated into any of the medical devices, including robotic and/or in vivo device, disclosed in the various patents and applications incorporated by reference above. Further, as also discussed above, the various implementations can be positioned on the end of a robotic arm.

Figure 23A:
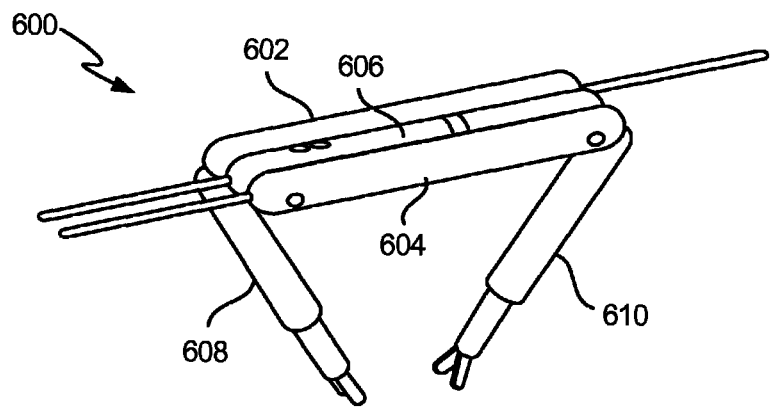
FIG. 23A is a perspective view of a robotic surgical device, according to one embodiment.
Figure 23B:
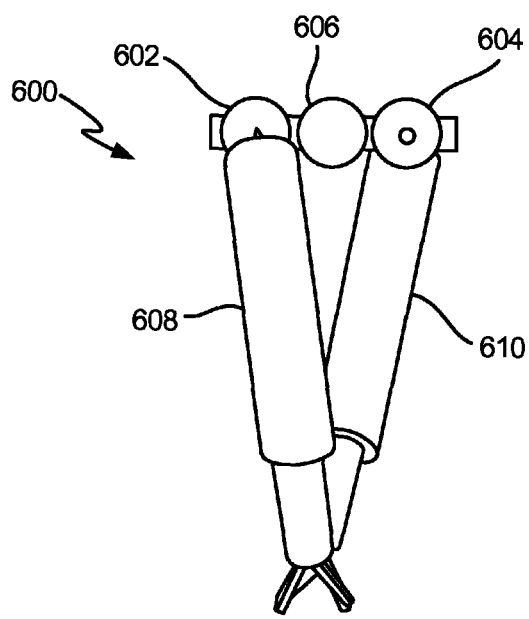
FIG. 23B is a side view of the robotic surgical device of FIG. 23A.
Figure 24A:
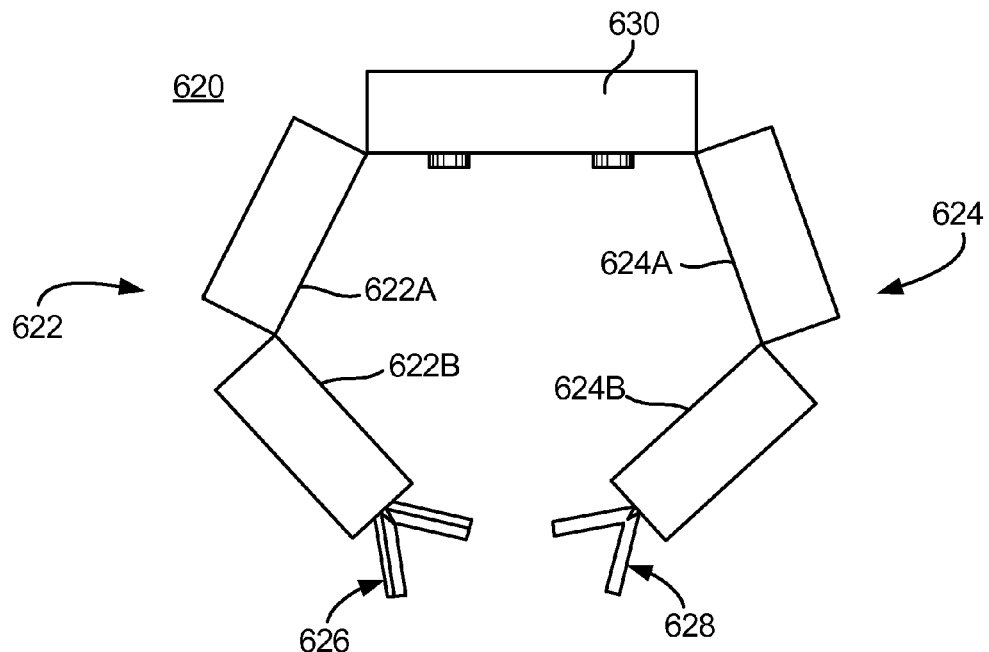
FIG. 24A is a front view of a robotic surgical device, according to another embodiment.
Figure 24B:
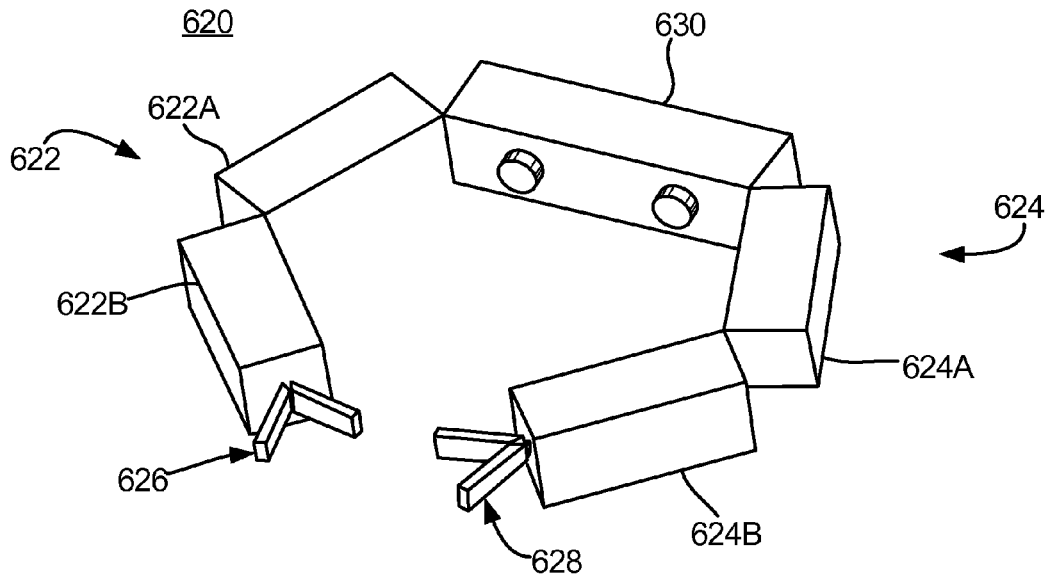
FIG. 24B is a perspective view of the robotic surgical device of FIG. 24A.

For example, any of the embodiments disclosed herein can be incorporated into the robotic device embodiments disclosed in U.S. Pat. No. 8,679,096 (which was incorporated herein above), including the devices depicted in FIGS. 23A-24B. FIGS. 23A and 23B depict a combination or modular medical device 600 having three modular components 602, 604, 606 coupled or attached to each other. More specifically, the device 600 has two robotic arm modular components 602, 604 and one robotic camera modular component 606 disposed between the other two components 602, 604. Each of the modular arm components 602, 604 have arms 608, 610. FIGS. 24A and 24B depict a robotic device 620 according to a further embodiment in which the device 620 has two arms 622, 624, each having a first link 622A, 624A and a second link 622B, 624B. Each arm 622, 624 also includes operational components 626, 628 that can be the same or different from one another. In addition, the device 620 has a body 630 that can have lighting and/or camera components and is disposed between and coupled to both arms 622, 624 as shown.

As another example, the various embodiments disclosed herein can also be incorporated into the robotic device embodiments disclosed in U.S. Application 61/506,384 (which was incorporated herein above), including the device shown in FIGS. 25A-25C. FIG. 25C depicts a robotic device 700 having a body 702 having two components 702A, 702B, wherein the body 702 is coupled to a support component 704 having a first support leg 706A and a second support leg 706B. Body component 702A is coupled to arm 708, and body component 702B is coupled to arm 710. Each of the arms 708, 710 has a first joint 708A 710A (each of which can also be referred to as a "shoulder join") that is coupled to the body components 702A, 702B. Each first joint 708A, 710A is coupled to a first link 708B, 710B that is rotatably coupled to a second link 708C, 710C. In addition, each arm 708, 710 also has an operational component 708D, 710D coupled to the second link 708C, 710C.

Figure 25A:
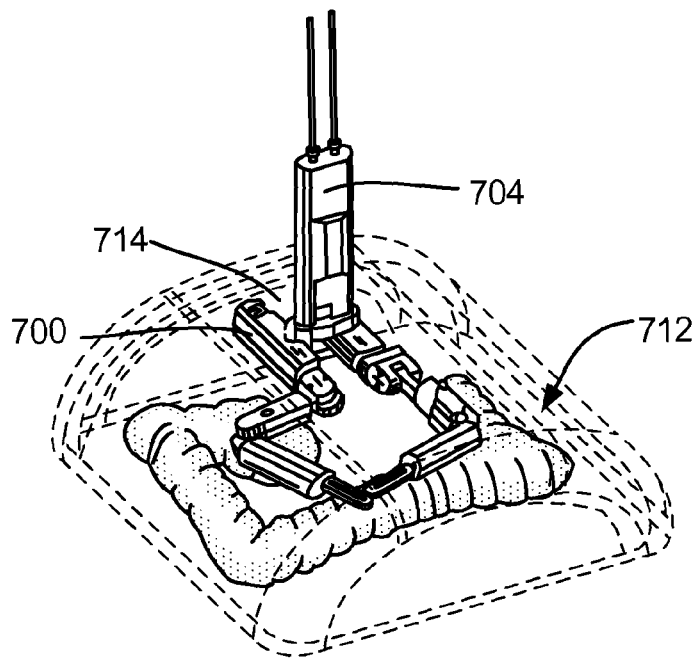
FIG. 25A is a perspective view of a robotic surgical device positioned in a patient's peritoneal cavity, according to one embodiment.
Figure 25B:
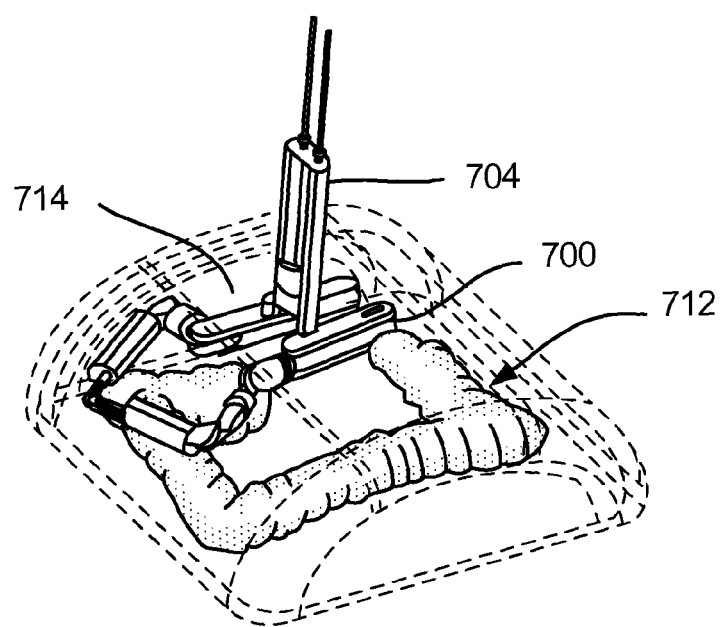
FIG. 25B is another perspective view of the robotic surgical device of FIG. 25A.
Figure 25C:
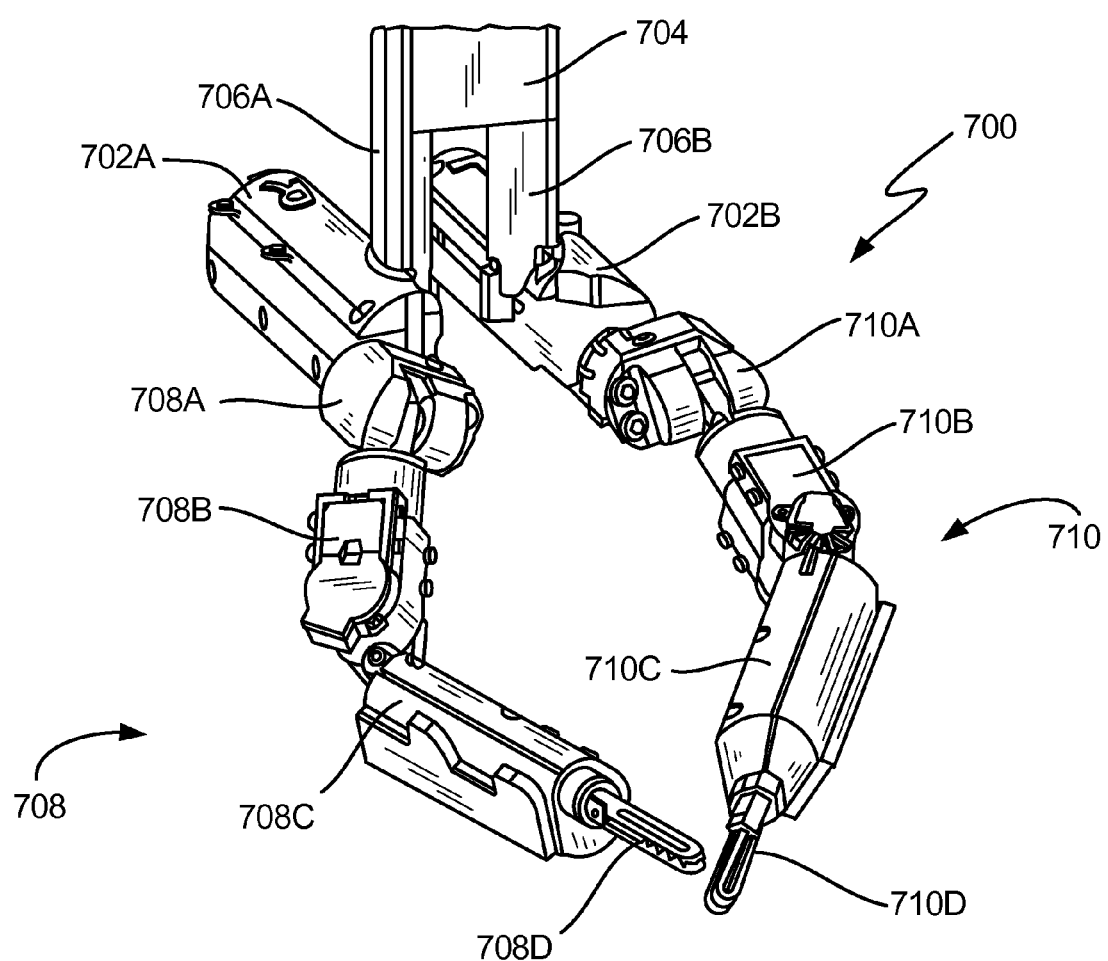
FIG. 25C is a perspective view of the robotic surgical device of FIG. 25A.

As best shown in FIGS. 25A and 25B, the support component XX is configured to maintain the device 700 in the desired positioned within a cavity 712 within the patient. The support component 704, which is coupled to the body 702, is disposed through an orifice or any Other kind of opening in the body cavity wall 714 such that the distal portion of the component 704 coupled to the body 702 is disposed within the body cavity 712 while the proximal portion is disposed outside the patient's body and can be attached to an external component (not shown) so as to provide stability or fixed positioning for the device 700.

Figure 26A:
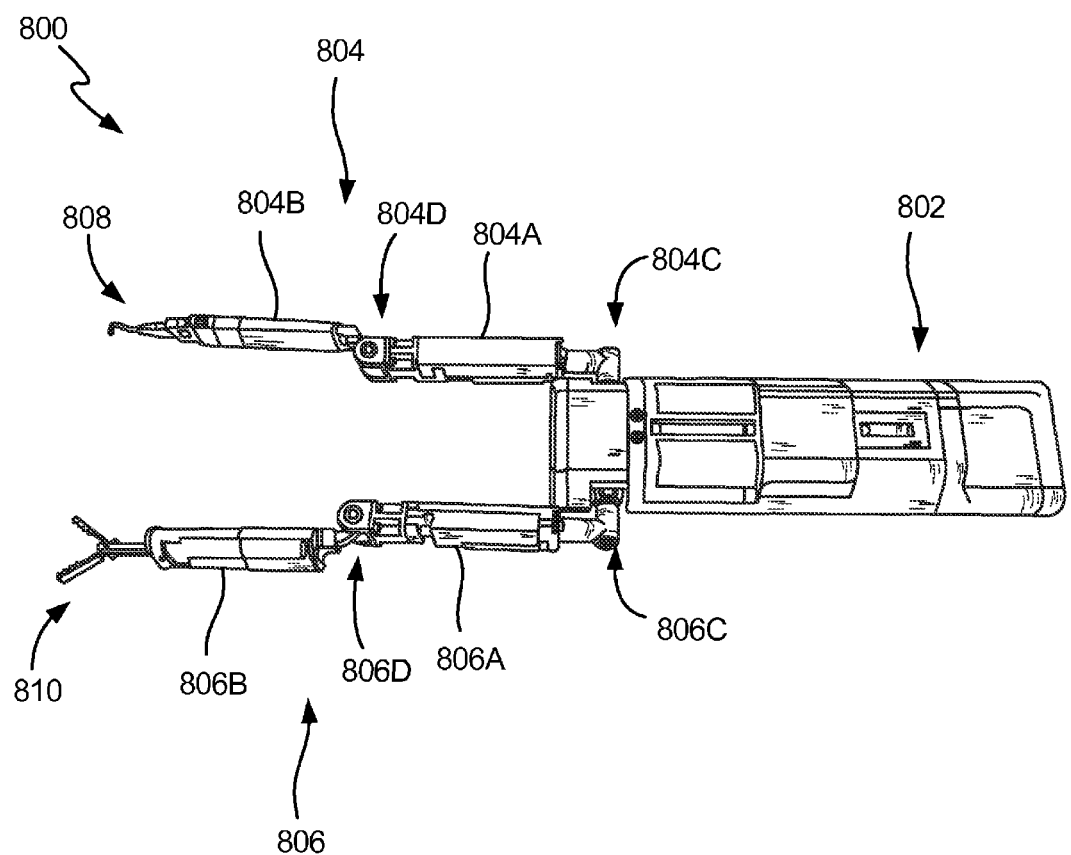
FIG. 26A is a front perspective view of a robotic surgical device, according to a further embodiment.
Figures 26B, 26C, 26D:
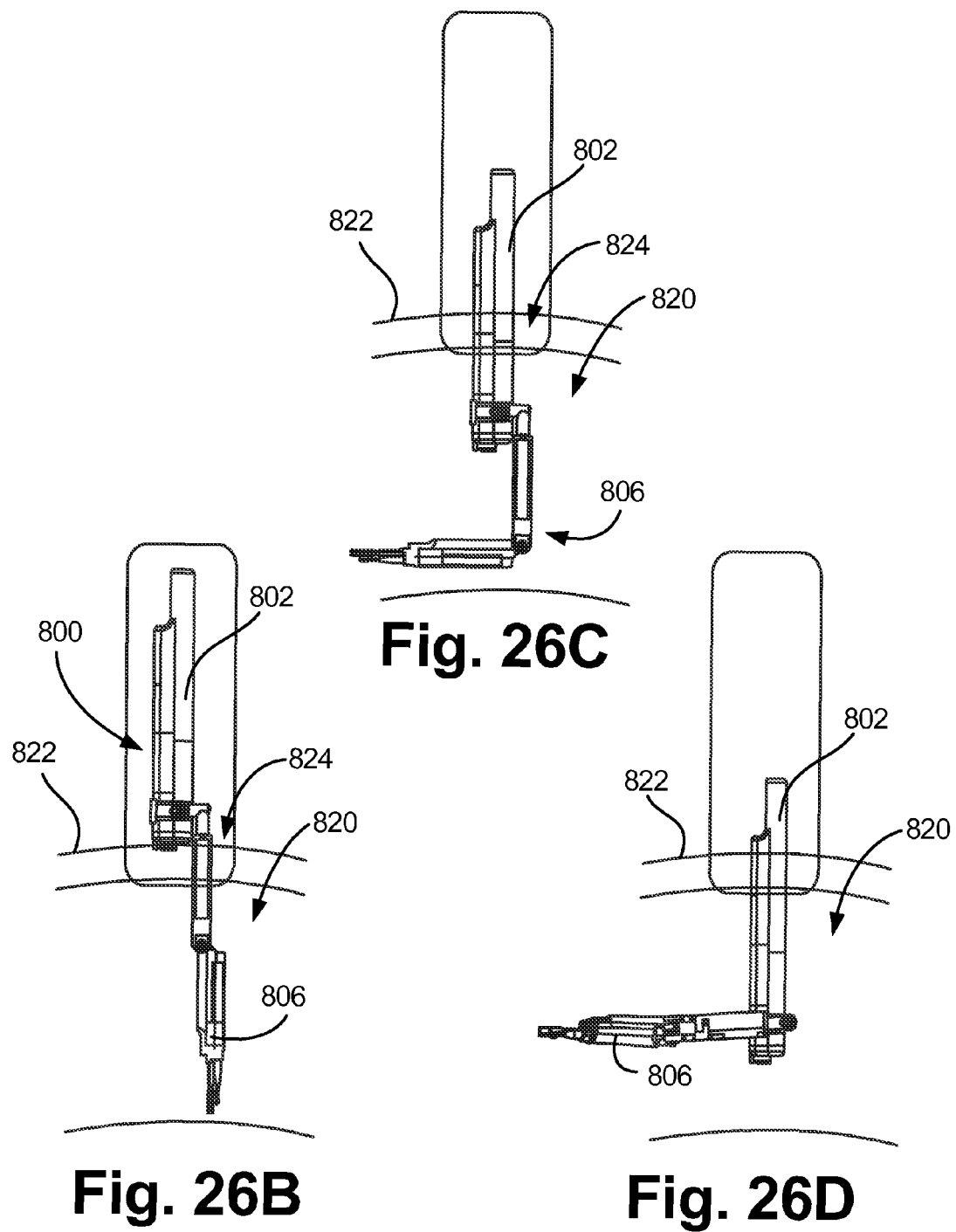
FIG. 26B is a side view of the robotic surgical device of FIG. 26A being inserted into a patient's body cavity, according to one embodiment.
FIG. 26C is a side view of the robotic surgical device of FIG. 26A being inserted into a patient's body cavity, according to one embodiment.
FIG. 26D is a side view of the robotic surgical device of FIG. 26A positioned a patient's body cavity, according to one embodiment.

In a further example, the various embodiments disclosed herein can also be incorporated into the robotic device embodiments disclosed in U.S. Application 61/640,879 (which was incorporated herein above), including the device depicted in FIGS. 26A-26D. FIG. 26A depicts a robotic device 800 having a main body 802, left arm 804, and right arm 806. Each of the arms 804, 806 is comprised of two segments: an upper arm (or first link) 804A, 806A, and a forearm (or second link) 804B, 806B, thereby resulting in each arm 804, 806 having a shoulder joint (or first joint) 804C, 806C and an elbow joint (or second joint) 804D, 806D. Each arm 804, 806 also has an end effector 808, 810. As shown in FIGS. 26B-26D, the device 800 can be positioned in or inserted into a cavity 820 of a patient such that, during a procedure, the arms 804, 806 are disposed entirely within the body cavity 820 while the device body 802 is positioned through an incision 824 in the wall 822 of the cavity 820.

Although the present invention has been described with reference to preferred embodiments, persons skilled in the art will recognize that changes may be made in form and detail without departing from the spirit and scope of the invention.

What is claimed is:

1. An in-vivo vessel sealing end effector, the end effector comprising:
   (a) an in vivo device body operably coupled to an arm of an in vivo robotic device, wherein the arm and the device body are configured to be positioned entirely within a cavity of a patient, the device body comprising:
      (i) a cautery component actuation motor;
      (ii) a cutting component actuation motor;
      (iii) a jaw actuation motor;
      (iv) a cautery component shaft disposed within the body and operably coupled to the jaw actuation motor; and
      (v) an electrical connection rotatably fixed to the cautery component shaft;
      (vi) a first slip ring coupled to the device body, wherein the first slip ring is configured to maintain electrical contact with electrical connection during rotation of the cautery component shaft;
   (b) a bipolar vessel cautery component operably coupled to the device body, the cautery component comprising:
      (i) a stationary jaw coupled to a distal end of the cautery component shaft;
      (ii) a mobile jaw pivotally coupled to the distal end of the cautery component shaft; and
      (iii) a cutting component operably coupled to the cutting component actuation motor, wherein the cautery component is operably coupled to the cautery component actuation motor, and
wherein the electrical connection is electrically coupled to one of the mobile jaw and the stationary jaw, and
(c) an external electrical source electrically coupled to the first slip ring.

2. The sealing end effector of claim 1, further comprising a second slip ring coupled to the device body, wherein the second slip ring is configured to maintain electrical contact with the cautery component shaft during rotation of the cautery component shaft, wherein the second slip ring is electrically coupled to the external electrical source.

3. The sealing end effector of claim 1, wherein the stationary jaw is configured to provide a stable base to support a vessel to be cauterized.

4. The sealing end effector of claim 1, further comprising a threaded collar rotatably coupled to the jaw actuation motor, wherein the collar is disposed around and threadably coupled with the cautery component shaft such that rotation of the collar causes axial movement of the cautery component shaft, thereby causing the mobile jaw to move between open and closed positions.

5. The sealing end effector of claim 1, wherein the cautery component actuation motor is rotatably coupled to the cautery component shaft such that rotation of the cautery component actuation motor causes rotation of the cautery component shaft, thereby causing rotation of the mobile and stationary jaws.

6. The sealing end effector of claim 1, wherein the cautery component is rotatable about an axis parallel with the cautery component shaft.

7. The sealing end effector of claim 1, wherein the overall length of the device body is under about 3 inches.

8. The sealing end effector of claim 1, wherein the overall length of the cautery component is under about 1.5 inches.

9. The sealing end effector of claim 1, further comprising:
(a) a collar rotatably coupled to the cutting component actuation motor;
(b) a translation pin fixedly coupled to the cutting component and operably coupled to the collar,
such that rotation of the collar causes axial movement of the cutting component between retracted and deployed positions.

10. An in-vivo vessel sealing end effector the end effector comprising:
(a) an in vivo device body operably coupled to an arm of an in vivo robotic device, wherein the arm and the device body are configured to be positioned entirely within a cavity of a patient, the device body comprising:
(i) a cautery component actuation motor;
(ii) a cutting component actuation motor;
(iii) a jaw actuation motor; and
(iv) a cautery component shaft disposed within the body and operably coupled to the jaw actuation motor;
(b) a bipolar vessel cautery component operably coupled to the device body, the cautery component comprising:
(i) a stationary jaw coupled to a distal end of the cautery component shaft;
(ii) a mobile jaw pivotally coupled to the distal end of the cautery component shaft;
(iii) a cutting component operably coupled to the cutting component actuation motor;
(iv) a first threaded collar rotatably coupled to the cutting component actuation motor; and
(v) a translation pin fixedly coupled to the cutting component and threadably coupled to the first threaded collar, such that rotation of the first threaded collar causes axial movement of the cutting component between retracted and deployed positions,
wherein the cautery component is operably coupled to the cautery component actuation motor.

11. The sealing end effector of claim 10, further comprising:
(a) an electrical connection rotatably fixed to the cautery component shaft, wherein the electrical connection is electrically coupled to one of the mobile jaw and the stationary jaw;
(b) a first slip ring coupled to the device body, wherein the first slip ring is configured to maintain electrical contact with electrical connection during rotation of the cautery component shaft;
(c) an external electrical source electrically coupled to the first slip ring; and
(d) a second slip ring coupled to the device body, wherein the second slip ring is configured to maintain electrical contact with the cautery component shaft during rotation of the cautery component shaft, wherein the second slip ring is electrically coupled to the external electrical source.

12. The sealing end effector of claim 10, further comprising a second threaded collar rotatably coupled to the jaw actuation motor, wherein the second collar is disposed around and threadably coupled with the cautery component shaft such that rotation of the second collar causes axial movement of the cautery component shaft, thereby causing the mobile jaw to move between open and closed positions.

13. The sealing end effector of claim 10, wherein the cautery component actuation motor is rotatably coupled to the cautery component shaft such that rotation of the cautery component actuation motor causes rotation of the cautery component shaft, thereby causing rotation of the mobile and stationary jaws.

14. The sealing end effector of claim 10, wherein the stationary jaw is configured to provide a stable base to support a vessel to be cauterized.

15. A robotic surgical device, comprising:
(a) a device body;
(b) at least one robotic arm operably coupled with the device body, wherein the at least one robotic arm is configured to be positioned entirely within a patient;
(c) a vessel-sealing end effector operably coupled to the at least one robotic arm, the end effector comprising:
(i) an end effector body comprising:
(A) a cautery component actuation motor;
(B) a cutting component actuation motor;
(C) a jaw actuation motor;
(D) a cautery component shaft rotatably disposed within the end effector body; and
(E) a first collar operably coupled to the jaw actuation motor, wherein the first threaded collar is disposed around and operably coupled to the cautery component shaft; and
(ii) a bipolar vessel cautery component operably coupled to the end effector body, the cautery component comprising:
(A) a stationary jaw coupled to a distal end of the cautery component shaft;
(B) a mobile jaw pivotally coupled to the distal end of the cautery component shaft; and
(C) a cutting component operably coupled to the cutting component actuation motor,
wherein the cautery component is operably coupled to the cautery component actuation motor.

16. The robotic surgical device of claim 15, wherein the stationary jaw is configured to provide a stable base to support a vessel to be cauterized.

17. The robotic surgical device of claim 15, wherein the first collar is threadably coupled with the cautery component shaft such that rotation of the collar causes axial movement of the cautery component shaft, thereby causing the mobile jaw to move between open and closed positions.

18. The robotic surgical device of claim 15, wherein the cautery component actuation motor is rotatably coupled to the cautery component shaft such that rotation of the cautery component actuation motor causes rotation of the cautery component shaft, thereby causing rotation of the mobile and stationary jaws.

19. The robotic surgical device of claim 15, further comprising:
(a) a second collar rotatably coupled to the cutting component actuation motor;
(b) a translation pin fixedly coupled to the cutting component and operably coupled to the second collar, such that rotation of the second collar causes axial movement of the cutting component between retracted and deployed positions.

20. The robotic surgical device of claim 15, further comprising:
(a) an electrical connection rotatably fixed to the cautery component shaft, wherein the electrical connection is electrically coupled to one of the mobile jaw and the stationary jaw;
(b) a first slip ring coupled to the device body, wherein the first slip ring is configured to maintain electrical contact with electrical connection during rotation of the cautery component shaft;
(c) an external electrical source electrically coupled to the first slip ring; and
(d) a second slip ring coupled to the device body, wherein the second slip ring is configured to maintain electrical contact with the cautery component shaft during rotation of the cautery component shaft, wherein the second slip ring is electrically coupled to the external electrical source.

* * * * *